United States Patent
Bae et al.

(10) Patent No.: US 12,325,698 B2
(45) Date of Patent: *Jun. 10, 2025

(54) PYRIMIDINE COMPOUNDS AND PHARMACEUTICAL COMPOSITIONS FOR PREVENTING OR TREATING CANCERS INCLUDING THE SAME

(71) Applicant: Hanmi Pharm. Co., Ltd., Hwaseong-Si (KR)

(72) Inventors: In Hwan Bae, Hwaseong-Si (KR); Ji Sook Kim, Hwaseong-Si (KR); Jae Yul Choi, Hwaseong-si (KR); Seok Jong Kang, Hwaseong-si (KR); Young Gil Ahn, Hwaseong-si (KR); Kwee Hyun Suh, Hwaseong-si (KR)

(73) Assignee: Hanmi Pharm. Co., Ltd., Hwaseong-Si (KR)

( * ) Notice: Subject to any disclaimer, the term of this patent is extended or adjusted under 35 U.S.C. 154(b) by 687 days.

This patent is subject to a terminal disclaimer.

(21) Appl. No.: 17/583,841

(22) Filed: Jan. 25, 2022

(65) Prior Publication Data

US 2023/0002358 A1   Jan. 5, 2023

Related U.S. Application Data

(60) Continuation of application No. 16/859,413, filed on Apr. 27, 2020, now Pat. No. 11,292,786, which is a division of application No. 16/396,233, filed on Apr. 26, 2019, now Pat. No. 10,870,639, which is a continuation of application No. PCT/KR2019/001737, filed on Feb. 13, 2019.

(30) Foreign Application Priority Data

Jul. 25, 2018   (KR) .................. 10-2018-0086768

(51) Int. Cl.
| | | |
|---|---|---|
| C07D 403/14 | (2006.01) | |
| A61P 35/02 | (2006.01) | |
| A61K 31/4025 | (2006.01) | |
| A61K 31/506 | (2006.01) | |

(52) U.S. Cl.
CPC ............ C07D 403/14 (2013.01); A61P 35/02 (2018.01); A61K 31/4025 (2013.01); A61K 31/506 (2013.01)

(58) Field of Classification Search
None
See application file for complete search history.

(56) References Cited

U.S. PATENT DOCUMENTS

| | | | |
|---|---|---|---|
| 8,461,170 B2 | 6/2013 | Aquila et al. | |
| 8,492,429 B2 | 7/2013 | Griffin et al. | |
| 9,796,712 B2 | 10/2017 | Huang et al. | |
| 10,280,154 B2 * | 5/2019 | Ham | A61K 31/506 |
| 10,519,141 B2 | 12/2019 | Ham et al. | |
| 10,870,639 B2 | 12/2020 | Bae et al. | |
| 11,292,786 B2 | 4/2022 | Bae et al. | |
| 2009/0318446 A1 | 12/2009 | Fischer et al. | |
| 2010/0056467 A1 | 3/2010 | Griffin et al. | |
| 2010/0104567 A1 | 4/2010 | Shiotsu et al. | |
| 2010/0249176 A1 | 9/2010 | Barrow et al. | |
| 2011/0009365 A1 | 1/2011 | Dubois et al. | |
| 2011/0015173 A1 | 1/2011 | Florjancic et al. | |
| 2011/0183975 A1 | 7/2011 | Goto et al. | |
| 2013/0137650 A1 | 5/2013 | Armstrong et al. | |
| 2017/0029413 A1 | 2/2017 | Holladay et al. | |
| 2017/0216302 A1 | 8/2017 | Seki | |
| 2017/0281566 A1 | 10/2017 | Ciceri et al. | |
| 2017/0355696 A1 | 12/2017 | Jiang | |
| 2018/0071290 A1 | 3/2018 | Cai et al. | |
| 2019/0031643 A1 | 1/2019 | Ham et al. | |
| 2019/0117649 A1 | 4/2019 | Bahceci et al. | |
| 2019/0125747 A1 | 5/2019 | Rezaei et al. | |
| 2019/0127353 A1 | 5/2019 | Ham et al. | |
| 2019/0298719 A1 | 10/2019 | Ferretti et al. | |
| 2019/0314380 A1 | 10/2019 | Falini et al. | |
| 2020/0031806 A1 | 1/2020 | Bae et al. | |
| 2020/0062775 A1 | 2/2020 | Xue et al. | |
| 2020/0206266 A1 | 7/2020 | Hudecek et al. | |
| 2020/0255410 A1 | 8/2020 | Bae et al. | |
| 2020/0360372 A1 | 11/2020 | Bahceci et al. | |
| 2022/0110913 A1 | 4/2022 | Bae et al. | |
| 2022/0354842 A1 | 11/2022 | Bae et al. | |
| 2024/0423979 A1 | 12/2024 | Kim et al. | |

FOREIGN PATENT DOCUMENTS

| | | |
|---|---|---|
| CN | 101111490 A | 1/2008 |
| CN | 101622015 A | 1/2010 |
| CN | 102471339 A | 5/2012 |
| CN | 108883109 A | 11/2018 |
| CN | 113166110 A | 7/2021 |
| EA | 201692261 A1 | 5/2017 |

(Continued)

OTHER PUBLICATIONS

Co-pending U.S. Appl. No. 18/251,827, inventors Bae; in Hwan et al., filed May 4, 2023.

[Author Unknown] "Khimicheskiy entsiklopedicheskiy slovar" (Chemical Encyclopedic Dictionary), Moscow: «Sovetskaya Entsiklopediya», 1983, pp. 130-131, and English translation of relevant portion, 7 pages.

Bastin et al., "Salt Selection and Optimisation Procedures for Pharmaceutical New Chemical Entities," Organic Process Research and Development (Jul. 19, 2000); 4(5): 427-435.

Belikov, V.G ,"Pharmaceutical Chemistry. Chapter 2.6 Relationship between the chemical structure, properties of substances and their effect on the body-M," MEDpress-inform, 2007, pp. 27-29, and English translation, 14 pages.

(Continued)

*Primary Examiner* — Craig D Ricci
(74) *Attorney, Agent, or Firm* — COOLEY LLP

(57) ABSTRACT

Provided are a pyrimidine compound represented by Formula 1, a method of preparing the compound, and a pharmaceutical use of the compound for the prevention or treatment of cancer.

8 Claims, No Drawings

(56) References Cited

FOREIGN PATENT DOCUMENTS

| | | |
|---|---|---|
| EA | 202191984 A1 | 11/2021 |
| EA | 039868 B1 | 3/2022 |
| EP | 2133095 A1 | 12/2009 |
| EP | 3514153 A1 | 7/2019 |
| EP | 3928780 A1 | 12/2021 |
| JP | 2008526824 A | 7/2008 |
| JP | WO2008111441 A1 | 6/2010 |
| JP | 2011500808 A | 1/2011 |
| JP | 2011510052 A | 3/2011 |
| JP | 2012521435 A | 9/2012 |
| JP | 2012533553 A | 12/2012 |
| JP | 2017510651 A | 4/2017 |
| JP | 2018535975 A | 12/2018 |
| JP | 2019531315 A | 10/2019 |
| JP | 6608565 B2 | 11/2019 |
| KR | 20080021126 A | 3/2008 |
| KR | 20090087094 A | 8/2009 |
| KR | 20090115866 A | 11/2009 |
| KR | 20170012766 A | 2/2017 |
| KR | 101755725 B1 | 7/2017 |
| KR | 20170101908 A | 9/2017 |
| KR | 20170123602 A | 11/2017 |
| KR | 20180086768 A | 8/2018 |
| KR | 20180088317 A | 8/2018 |
| KR | 20180117710 A | 10/2018 |
| KR | 20180124055 A | 11/2018 |
| KR | 101954370 B1 | 3/2019 |
| KR | 20190084292 A | 7/2019 |
| KR | 20200016567 A | 2/2020 |
| KR | 102110573 B1 | 5/2020 |
| KR | 20200102948 A | 9/2020 |
| MX | 2019008808 A | 9/2019 |
| TW | 201829396 A | 8/2018 |
| WO | WO-2006075152 A1 | 7/2006 |
| WO | WO-2006135639 A1 | 12/2006 |
| WO | WO-2008067280 A2 | 6/2008 |
| WO | WO-2009054983 A1 | 4/2009 |
| WO | WO-2009109710 A1 | 9/2009 |
| WO | WO-2010049731 A1 | 5/2010 |
| WO | WO-2010051781 A1 | 5/2010 |
| WO | WO-2010111172 A1 | 9/2010 |
| WO | WO-2011008915 A1 | 1/2011 |
| WO | WO-2011162515 A2 | 12/2011 |
| WO | WO-2013014448 A1 | 1/2013 |
| WO | WO-2013146963 A1 | 10/2013 |
| WO | WO-2014155300 A2 | 10/2014 |
| WO | WO-2015154038 A1 | 10/2015 |
| WO | WO-2015154039 A2 | 10/2015 |
| WO | WO-2015154039 A3 | 12/2015 |
| WO | WO-2016029839 A1 | 3/2016 |
| WO | WO-2015154039 A8 | 10/2016 |
| WO | WO-2017083592 A1 | 5/2017 |
| WO | WO-2017157813 A1 | 9/2017 |
| WO | WO-2017170348 A1 | 10/2017 |
| WO | WO-2018002217 A1 | 1/2018 |
| WO | WO-2018118842 A1 | 6/2018 |
| WO | WO-2018134213 A1 | 7/2018 |
| WO | WO/2018/139903 * 8/2018 ........... C07D 403/14 |
| WO | WO-2018139903 A1 | 8/2018 |
| WO | WO-2018156578 A1 | 8/2018 |
| WO | WO-2019164846 A1 | 8/2019 |
| WO | WO-2020014643 A1 | 1/2020 |
| WO | WO-2020022600 A1 | 1/2020 |
| WO | WO-2020171646 A1 | 8/2020 |
| WO | WO-2020171649 A1 | 8/2020 |
| WO | WO-2020262974 A1 | 12/2020 |
| WO | WO-2021066443 A1 | 4/2021 |
| WO | WO-2021159993 A1 | 8/2021 |
| WO | WO-2022098083 A1 | 5/2022 |
| WO | WO-2023068858 A1 | 4/2023 |
| WO | WO-2024096708 A1 | 5/2024 |
| WO | WO-2024124199 A1 | 6/2024 |
| WO | WO-2024248513 A1 | 12/2024 |

OTHER PUBLICATIONS

Kummerer, K., et al., "Pharmaceuticals in the Environment," Annual Review of Environment and Resources (2010); vol. 35, pp. 57-75. Epub Aug. 18, 2010.
Pokrovsky, V.I., "Small Medical Encyclopedia," Medicine, 1996, V5, pp. 90-96, and English translation of relevant portion, 12 pages.
International Preliminary Report on Patentability for International Patent Application No. PCT/KR2021/015794 dated May 8, 2023, and English translation, 4 pages.
International Search Report and English translation for International Patent Application No. PCT/KR2021/015794 mailed Feb. 10, 2022, and English translation, 9 pages.
Written Opinion for International Patent Application No. PCT/KR2021/015794 mailed Feb. 10, 2022, and English translation 6 pages.
Daver, N., et al., "Targeting FLT3 Mutations in AML: Review of Current Knowledge and Evidence," Leukemia (Jan. 16, 2019); 33(2): 299-312. Epub Jan. 16, 2019.
Extended European Search Report for European Application No. 20759712.1 dated Nov. 4, 2022, 10 pages.
Edwards, D., et al., "CPX-351 works synergistically in combination with FLT3 inhibitors against AML with FLT3-ITD", Cancer Research Jul. 2017; vol. 77, No. Suppl. 13, p. 1087, & Annual Meeting of the American Association for Cancer Research (AACR); Washington, DC, USA; Apr. 1-5, 2017, 2 pages.
Extended European Search Report for European Application No. EP20200833623 dated Jun. 5, 2023, 9 pages.
Schittenhelm, M., et al., "The FLT3 1-15 inhibitor tandutinib (formerly MLN518) has sequence-independent synergistic effects with cytarabine and daunorubicin", Cell Cycle. Aug. 15, 2009; 8(16): 2621-2630. Epub Aug. 24, 2009.
Brinton, L.T. et al., "Synergistic effect of BCL2 and FLT3 co-inhibition in acute myeloid leukemia", J Hematol Oncol, 2020;13:139, 10 pages; doi:10.1186/s13045-020-00973-4.
Edwards et al., "Effective Combination of CPX/351 with FLT3 Inhibitors in AML Blasts Harboring the FLT3-ITD Mutation", Blood Dec. 2, 2016; 128 (22): 5124, 2 pages.
Extended European Search Report for European Patent Application No. 21889548.0 dated Sep. 12, 2024, 9 pages.
International Preliminary Report on Patentability for International Application No. PCT/KR2022/016095, including Notification of Transmittal, mailed May 2, 2024; 8 pages.
International Preliminary Report on Patentability for International Patent Application No. PCT/KR2019/001737, with Notification of Transmittal, mailed Feb. 4, 2021, 9 pages.
International Search Report and Written Opinion for International Application No. PCT/KR2022/016095, with Notification of Transmittal, mailed Jan. 27, 2023, 12 pages.
International Search Report and Written Opinion for International Application No. PCT/US2023/083227, with Notification of Transmittal, mailed Apr. 2, 2024, 13 pages.
International Search Report and Written Opinion for International Application No. PCT/KR2023/017598, including Notification of Transmittal, dated Feb. 14, 2024, 16 pages.
International Search Report and Written Opinion for International Application No. PCT/KR2024/007424, with Notification of Transmittal, mailed Sep. 11, 2024, 16 pages.
Invitation to Pay Additional Fees for International Application No. PCT/US2023/083227, mailed Feb. 13, 2024; 3 pages.
Luppi, Mario, et al., "Novel Agents for Acute Myeloid Leukemia", Cancers, Nov. 9, 2018; 10(11):429, 18 pages.
Zhu, R. et al., "FLT3 tyrosine kinase inhibitors synergize with BCL-2 inhibition to eliminate FLT3/ITD acute leukemia cells through BIM activation", Signal Transduction and Targeted Therapy, 2021, [Epub] May 24, 2021; 6:186, doi10.1038/s41392-021-00578-4; 11 pages.
Chang, E. et al., "The combination of FLT3 and DNA methyltransferase inhibition is synergistically cytotoxic to FLT3/ITD acute myeloid leukemia cells". Leukemia, Dec. 21, 2015, vol. 30, No. 5, pp. 1025-1032.

(56) References Cited

OTHER PUBLICATIONS

Ueno, Y. et al., "Gilteritinib (ASP2215), a Novel FLT3/AXL Inhibitor: Preclinical Evaluation in Combination with Azacitidine in Acute Myeloid Leukemia". Blood, Dec. 2, 2016, vol. 128, No. 22, p. 2830, 4 pages.
Wu, M. et al., "FLT3 inhibitors in acute myeloid leukemia". Journal of Hematology & Oncology, Dec. 4, 2018, vol. 11, No. 1, Article No. 133, 11 pages.
Advani, Anjali S., "FL T3 and Acute Myelogenous Leukemia: Biology, Clinical Significance and Therapeutic Applications", Current Pharmaceutical Design, 2005, vol. 11, No. 26, pp. 3449-3457.
Araki, Shinsuke et al., "Inhibitors of CLK Protein Kinases Suppress Cell Growth and Induce Apoptosis by Modulating Pre-mRNA Splicing", PLOS One, Jan. 12, 2015, vol. 10, 18 pages.
Benson et al., "Identification of Telmisartan as a Unique Angiotensin II Receptor Antagonist With Selective PPARγ-Modulating Activity", Hypertension, May 2004, vol. 43, pp. 993-1002.
Buglio, D., et al., "Essential Role of TAK1 in Regulating Mantle Cell Lymphoma Survival," Blood, 2012, vol. 120(2), pp. 347-355.
Carter et al., "Synergistic Targeting of AML Stem/Progenitor Cells With IAP Antagonist Birinapant and Demethylating Agents", JNCI, Feb. 5, 2014, 106(2):djt440, 12 pages.
Extended European Search Report for European Patent Application No. 18744290.0 dated Mar. 31, 2020, 7 pages.
Extended European Search Report for European Patent Application No. 19841611.7 dated Mar. 17, 2022, 11 pages.
Extended European Search Report for European Patent Application No. 20201112.8 dated Feb. 5, 2021, 6 pages.
Huang, et al., "Synthesis and biological study of 2-amino-4-aryl-5-chloropyrimidine analogues as inhibitors of VEGFR-2 and cyclin dependent kinase 1 (CDK1)". Bioorganic & Medicinal Chemistry Letters (Apr. 15, 2007); 17(8): 2179-2183. Epub Feb. 2, 2007.
International Preliminary Report on Patentability for International Patent Application No. PCT/KR2020/002536 mailed Aug. 10, 2021, and English translation, 10 pages.
International Preliminary Report on Patentability for International Patent Application No. PCT/KR2020/008258 mailed Dec. 28, 2021, and English translation, 8 pages.
International Search Report and Written Opinion for International Patent Application No. PCT/KR2020/013188 dated Jun. 4, 2020, and English translation of ISR, 15 pages.
International Search Report for International Patent Application No. PCT/KR2018/001193 dated May 2, 2018, and English translation, 7 pages.
International Search Report for International Patent Application No. PCT/KR2019/001737 mailed May 8, 2019, 4 pages.
International Search Report for International Patent Application No. PCT/KR2020/002536 dated Jun. 4, 2020, and English translation, 5 pages.
International Search Report for International Patent Application No. PCT/KR2020/008258 dated Sep. 22, 2020, and English translation, 7 pages.
Khurana and Shafer, "MDM2 antagonists as a novel treatment option for acute myeloid leukemia: perspectives on the therapeutic potential of idasanutlin (RG7388)". Onco Targets Ther. (2019); 12: 2903-2910. Epub Apr. 16, 2019.
Kiyoi et al., "FLT3 mutations in acute myeloid leukemia: Therapeutic paradigm beyond inhibitor development.". Cancer Science, Feb. 2020; 111(2): 312-322.
Kliche, Stefanie et al., "VEGF Receptor Signaling and Endothelial Function", IUBMB Life, 2001, vol. 51, pp. 61-66, 6 pages.
Konig et al., "The Combination of FL T3 Inhibition and Hypomethylation Confers Synergistic Anti-Leukemic Effects on FL T3/ITD Positive AML Cell Lines and Primary Cells", Blood, Nov. 15, 2013, 122(21): 3965, 3 pages.

Lee et al., "FL T3MutationsConfer Enhanced Proliferation and Survival Properties to Multipotent Progenitors in a Murine Model of Chronic Myelomonocytic Leukemia", Cancer Cell, Oct. 2007, vol. 12, pp. 367-380.
Liu et al., "Syk inhibitors in clinical development for hematological malignancies", Journal of Hematology and Oncology, 2017, 10: 145, 7 pages.
McMahon et al., "Clonal Selection with RAS Pathway Activation Mediates Secondary Clinical Resistance to Selective FLT3 Inhibition in Acute Myeloid Leukemia". Cancer Discov, 2019, 9 (8): 1050-1063.
Melnikova, Irena et al., "Targeting protein kinases", Nature Reviews Drug Discovery, Dec. 2004, pp. 993-994, 2 pages.
Moore et al., "Selective FL T3 inhibition of FL T3-ITD t acute myeloid leukaemia resulting in secondary D835Y mutation: a model for emerging clinical resistance patterns", Leukemia, 2012, pp. 1462-1470.
Paccez, Juliano D. et al., "The receptor tyrosine kinase Axl in cancer: biological functions and therapeutic implications", International Journal of Cancer, 2014, 39 pages, vol. 134.
Seipel et al., "Pabst T. MDM2-and FLT3-inhibitors in the treatment of FLT3-ITD acute myeloid leukemia, specificity and efficacy of NVP-HDM201 and midostaurin". Haematologica, Nov. 2018; 103(11): 1862-1872. Pre-published: Jul. 5, 2018.
Simons, Michael et al., "Mechanisms and regulation of endothelial VEGF receptor signalling", Nature Reviews Molecular Cell Biology, Oct. 2016, vol. 17, pp. 611-625, 15 pages.
Smith et al., "Validation of ITD mutations in FLT3 as a therapeutic target in human acute myeloid leukaemia", Nature, 2012, vol. 000, p. 1-6.
Sun, Xianglan et al., :"The regulation and function of the NUAK family", Journal of Molecular Endocrinology, 2013, 9 pages, vol. 51.
Ueno, et al., "Evaluation of gilteritinib in combination with chemotherapy in preclinical models of FLT3-ITD+ acute myeloid leukemia". Oncotarget (2019); 10(26): 2530-2545.
Wang et al., "Crenolanib, a Type I FLT3 TKI, Can be Safely Combined with Cytarabine and Anthracycline Induction Chemotherapy and Results in High Response Rates in Patients with Newly Diagnosed FLT3 Mutant Acute Myeloid Leukemia (AML)". Blood. Jan. 1, 2016; 128(22): 1071, 4 pages.
Weisberg et al., "Drug resistance in mutant FL T3-positive AML", Oncogene, Sep. 2010, 29(37): 5120-5134.
Weisberg et al., "Potentiation of antileukemic therapies by Smac mimetic, LBW242: effects on mutant FL T3-expressing cells", Molecular Cancer Therapeutics, Jul. 2007, 6(7): 1951-1961.
Written Opinion for International Patent Application No. PCT/KR2018/001193 dated May 2, 2018, and English translation, 12 pages.
Written Opinion for International Patent Application No. PCT/KR2019/001737 mailed May 8, 2019, 4 pages.
Written Opinion for International Patent Application No. PCT/KR2020/002536 dated Jun. 4, 2020, and English translation, 16 pages.
Written Opinion for International Patent Application No. PCT/KR2020/008258 dated Jun. 4, 2020, and English translation, 13 pages.
Wu, Xiaoliang et al., "AXL kinase as a novel target for cancer therapy", Oncotarget, Oct. 16, 2014, vol. 20, No. 5, pp. 9546-9563, 18 pages.
Yamada et al., IL-1 Induced Chemokine Production Through the Association of Syk with TNF Receptor-Associated Factor-6 in Nasal Fibroblast Lines, Journal of Immunology, Jul. 1, 2001, pp. 283-288.
Zhao et al., "1737The regulation of MDM2 oncogene and its impact on human cancers". Acta Biochim Biophys Sin. Mar. 1, 2014; 46(3): 180-189.

* cited by examiner

PYRIMIDINE COMPOUNDS AND PHARMACEUTICAL COMPOSITIONS FOR PREVENTING OR TREATING CANCERS INCLUDING THE SAME

CROSS-REFERENCE TO RELATED APPLICATION

This application is a Continuation of U.S. application Ser. No. 16/859,413 filed Apr. 27, 2020, which is a Divisional of U.S. application Ser. No. 16/396,233 filed Apr. 26, 2019, which is a Continuation of International Application No. PCT/KR2019/001737, filed on Feb. 13, 2019, which claims the benefit of Korean Patent Application No. 10-2018-0086768, filed on Jul. 25, 2018, in the Korean Intellectual Property Office, the disclosure of which is incorporated herein in its entirety by reference.

BACKGROUND

1. Field

The present disclosure relates to novel pyrimidine compounds, methods of preparing the same, and pharmaceutical use thereof.

2. Description of the Related Art

Kinases mediate a reaction in which a phosphate group from high-energy molecules, in particular, ATP, is transferred to a substrate. Kinases stabilize phosphoric anhydride bonds, and locate the substrate and the phosphate group at a specific position to increase a reaction rate. In most cases, the transition state resulting from the interaction with a phosphate group having a negative charge is electrostatically stabilized through surrounding amino acids having a positive charge, and some kinases may be coordinated with the phosphate group through a metal cofactor.

Kinases can be classified as, for example, protein kinases, lipid kinases, and carbohydrate kinases, according to the substrate and characteristics. Proteins, lipids, or carbohydrates may vary in their activity, reactivity, ability to bind to other molecules, etc., depending on the phosphorylation state. Kinases affect intracellular signal transduction and regulate complex biological mechanisms within cells. Due to phosphorylation, some molecules may have enhanced or reduced activities, and their ability to interact with other molecules may be controlled. Because many kinases respond to environmental conditions or signals, cells may control intracellular molecules by using kinases, depending on the situation. As such, kinase plays a crucial role in cell growth, differentiation, proliferation, survival, metabolism, signal transduction, cell transport, secretion, and many other cellular reaction pathways.

Kinases have been found in a variety of species including bacteria, fungi, insects, and mammals, and 500 or more kinases have been found in humans to date.

Protein kinases may increase or decrease the activity of a protein, become a marker for stabilization or degradation, place a protein in a specific cell compartment, or initiate or disturb interactions of a protein with other proteins. Protein kinases are known to account for the majority of kinases and are considered to be an important research target. Protein kinases regulate, together with phosphatase, proteins and enzymes as well as cell signal transduction. Although cell proteins are subject to numerous covalent bonds, not many of these bonds are reversible. Accordingly, it can be said that phosphorylation of proteins has a regulatory function. Protein kinases may often have multiple substrates, and sometimes, a particular protein may act as a substrate for at least one kinase. For this reason, protein kinases are named using factors that regulate their activities. For example, a calmodulin-dependent protein kinase is regulated by calmodulin. In some cases, kinases may be classified as sub-groups. For example, type I and type II cyclic AMP-dependent protein kinases include identical enzyme subunits, but their regulatory subunits binding to cyclic AMP are different from each other.

A protein kinase is an enzyme that catalyzes the phosphorylation of the hydroxy group located in tyrosine, serine, and threonine residues of proteins and plays an important role in signaling growth factors that induce cell growth, differentiation, and proliferation (Melnikova, I. et al., Nature Reviews Drug Discovery, 3 (2004), 993), and it is reported that abnormal expression or mutation of a specific kinase frequently occurs in cancer cells.

As one of the ways that cells recognize external stimuli, recognition via tyrosine kinase, which is a receptor in the cell membrane, may be used. A receptor tyrosine kinase (RTK) consists of an extracellular part exposed to the outside of a cell, an intracellular part exposed to the intracellular cytoplasm, and a transmembrane part passing through the plasma membrane between the extracellular part and the intracellular part. The extracellular part of the receptor is the part to which a specific ligand binds, and the intracellular part functions to transmit the activation signal of the receptor activated by the ligand into the cell. The RTK has a domain having tyrosine kinase activity at the C-terminal region exposed inside the cell, and when a specific ligand attaches to the extracellular part, the kinase enzyme of the C-terminal tyrosine kinase domain exposed to the cytoplasmic portion of the receptor protein is activated, and the two RTKs cross-phosphorylate the tyrosines at the C-terminals of the neighboring RTKs. This phosphorylation process of tyrosine is the most important process in the transmission of signals corresponding to extracellular stimulation into cells. There are many known receptors that have tyrosine kinase activities for transmitting extracellular stimuli into cells based on this mechanism. Examples of such receptors are FLT3, VEGFR, and SYK.

From among them, FMS-like tyrosine kinase 3 (FLT3), which is a receptor tyrosine kinase, is normally expressed in hematopoietic progenitor cells by hematopoietic blast cells and plays an important role in the expression of normal stem cells and the immune system. Abnormal overexpression and mutations of FLT3 are often found in patients with leukemia. In particular, various mutations of FLT3, such as D835V, D835Y and internal tandem duplication (ITD), are found in acute myelogenous leukemia (AML). AML is a hematopoietic stem cell disorder characterized by abnormal proliferation and differentiation of blast cells in myeloid and peripheral blood. FLT3 has recently been regarded as one of the most important targets in the therapeutic aspects of AML.

RAS and p53 gene mutations in adult AML are reported to be about 20% and 5% of adult AML, respectively, whereas FLT3 gene mutations are found in about 30% of adult AML. The most typical problem with AML is that FLT3 mutations, which cause poor prognosis, are activated. FLT3 mutations are classified into two types: one is internal tandem duplications (ITD) in the juxtamembrane domain and the other is point mutations in the tyrosine kinase domain (TKD). About 23% of early AML patients experience the activation of FLT3-ITD, the most frequently found mutation. Patients with an ITD mutation show poor prognosis and high recurrence rates. Another major FLT3 mutation is the FLT3 TKD mutation, which accounts for about 7% of the initial AML cases. Point mutations in residues of aspartate 835 (D835), which are replaced by various amino acids, are one of the most frequently occurring mutations, although they occur less than ITD mutations. In addition, another major activation method of FLT3 in AML is the overexpression of the wild type FLT3 protein.

The activation of ITD mutations in FLT3 occurs in about 20% of patients with acute myelogenous leukemia, which is associated with poor prognosis. Studies have shown that FLT3-ITD is a driver lesion that causes the pathogenesis of malignancy and can be an effective therapeutic target in human AML (Non-patent document 1). Mutations in the FLT3 gene frequently occur in AML, and are usually accompanied by ITD mutations in a juxtamembrane domain coding region or point mutations in the tyrosine kinase domain (TKD). FLT3-ITD mutations and FLT3-TKD mutations cause ligand-independent proliferation due to dimerization of components and activation of the FLT3 receptor. The high mutation rate of FLT3-ITD with respect to wild-type allele is associated with poor prognosis in adults and children (Non-patent document 2). Other types of leukemia, such as chronic myelomonocytic leukemia (CMML), may also have an activation mutation of FLT3. Thus, FLT3 with activated mutations is an important target for several cancer types (Non-patent document 3 and Non-patent document 4).

Vascular endothelial growth factor receptor (VEGFR) is a kinase known to be involved in the regulation of the angiogenesis process. Solid tumors require more nutrients and oxygen than normal tissues. Therefore, insufficiency of blood supply occurs compared to normal states, and the overexpression or activation of VEGFR induces neovascularization, being involved in the angiogenesis required for the growth and proliferation of tumor cells (Non-patent document 5). Therefore, various clinical studies for the treatment of tumors through inhibition of angiogenesis have been performed, and several promising results have been obtained. In addition, VEGF plays an important role in blood cancer and is overexpressed in various malignant solid tumors. The overexpression of VEGF is known to have a high correlation with disease progression of malignant tumors. VEGFRs are classified according to subtypes including VEGFR-1, VEGFR-2, and VEGFR-3. VEGFR-2 (KDR) is a typical target for tumor diseases having VEGFR expression. Representative diseases caused by the overexpression of VEGFR-2 are lung cancer, breast cancer, non-Hodgkin's lymphoma, ovarian carcinoma, pancreatic cancer, etc. VEGF, which is a ligand of VEGFR, may have angiogenic activity and promote tumor growth by a direct pro-survival effect in tumor cells (Non-patent document).

Spleen tyrosine kinase (SYK) is mainly expressed in blood cells, and plays an important role in the signal transduction pathways of other immunoreceptors such as B-cell receptors and mast cells. SYK is expressed in non-hematopoietic cells such as nerve cells and vascular endothelial cells. Recent studies show that SYK acts in oxidization of stimuli of various cells including IL-1, TNF-α, and ITGB1. SYK is known to be a good potential target for a variety of hematologic malignant tumor, autoimmune diseases, and other inflammatory responses (Non-patent document 7 and Non-patent document 8).

PRIOR ART DOCUMENT

Non-Patent Document (Non-patent document 1) Catherine et al., Nature, 2012, 485: 260-263

(Non-patent document 2) A S Moore et al., Leukemia, 2012, 26: 1462-1470
(Non-patent document 3) Cancer Cell, (2007), 12: 367-380
(Non-patent document 4) Current Pharmaceutical Design (2005), 11: 3449-3457
(Non-patent document 5) Kliche, S. et al., J., Life, 52, (2001), 61
(Non-patent document 6) Simons, M. et al., Nature Reviews Molecular Cell Biology, 17, (2016), 611
(Non-patent document 7) Liu et al., Journal of Hematology & Oncology (2017) 10:145
(Non-patent document 8) Yamada T et al., J. Immunol., (2001) 167, 283-288

SUMMARY

Provided are novel pyrimidine compounds having kinase inhibitory activity.

Provided are methods of preparing the pyrimidine compounds.

Provided are pharmaceutical uses of the pyrimidine compounds.

Additional aspects will be set forth in part in the description which follows and, in part, will be apparent from the description, or may be learned by practice of the presented embodiments.

According to an aspect of an embodiment, provided is a compound selected from a compound represented by Formula 1, and a stereoisomer, tautomer, solvate, or pharmaceutically acceptable salt thereof:

[Formula 1]

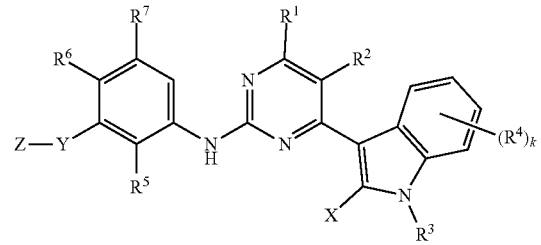

wherein, in Formula 1,
$R^1$ may be hydrogen, a halogen, a hydroxy group, a $C_1$-$C_4$ alkoxy group, or —$NR_aR_b$,
wherein $R_a$ and $R_b$ may each independently be hydrogen or a $C_1$-$C_4$ alkyl group;
$R^2$ may be hydrogen, a halogen, a cyano group, a nitro group, an amino group, a carboxamide group, a formyl group, a halo $C_1$-$C_4$ alkyl group, or a $C_1$-$C_4$ alkyl group;
$R^3$ may be hydrogen, a halogen, a hydroxy group, a halo $C_1$-$C_4$ alkyl group, a $C_1$-$C_4$ alkyl group, a $C_2$-$C_4$ alkenyl group, or a $C_2$-$C_4$ alkynyl group;
$R^4$ may each independently be hydrogen, a halogen, a hydroxy group, a cyano group, a nitro group, an amino group, —S(=O)$_l$—$R_c$, a halo $C_1$-$C_4$ alkyl group, a $C_1$-$C_4$ alkoxy group, a hydroxy $C_1$-$C_4$ alkyl group, a $C_1$-$C_4$ alkyl group, a $C_2$-$C_4$ alkenyl group, a $C_2$-$C_4$ alkynyl group, —$NR_dR_e$, —$CO_2R_e$, or —CO—$NR_dR_e$,
wherein $R_c$ is a $C_1$-$C_4$ alkyl group or —$NR_dR_e$,
$R_d$ and $R_e$ are each independently hydrogen or a $C_1$-$C_4$ alkyl group, and
l may be an integer from 0 to 2;
k may be an integer from 0 to 4;

$R^5$ and $R^6$ may each independently be hydrogen, a halogen, a hydroxy group, a nitro group, an amino group, a $C_1$-$C_4$ alkoxy group, or a $C_1$-$C_4$ alkyl group;

$R^7$ may be a hydroxy $C_1$-$C_4$ alkyl group, a $C_1$-$C_4$ alkyl group, a $C_2$-$C_4$ alkenyl group, a $C_2$-$C_4$ alkynyl group, a $C_3$-$C_7$ cycloalkyl group, or a $C_3$-$C_9$ heterocycloalkyl group, wherein the $C_3$-$C_7$ cycloalkyl group or the $C_3$-$C_9$ heterocycloalkyl group may be unsubstituted or substituted with a halogen, a $C_1$-$C_4$ alkyl group or a halo $C_1$-$C_4$ alkyl group; and X is H or OH, wherein, when X is OH, the compound represented by Formula 1 may include a tautomeric structure represented by Formula 2, Formula 2

$R^3$, $R^4$, and k in Formula 2 may be the same as described in connection with Formula 1;

Y is $-(CH_2)_m-$, $-(CH_2)_m-O-(CH_2)_n-$, $-(CH_2)_m-CO-(CH_2)_n-$, $-(CH_2)_m-NR^8-(CH_2)_n-$, or $-(CH_2)_m-SO_2-(CH_2)_n-$, wherein $R^8$ is hydrogen or a $C_1$-$C_4$ alkyl group, m and n are each independently an integer from 0 to 2; and Z is represented by Formula 3;

Formula 3 wherein, in Formula 3,

A is a $C_3$-$C_{10}$ cycloalkyl group or a $C_2$-$C_{11}$ heterocycloalkyl group;

$R^9$ is halogen, a hydroxy group, a cyano group, a nitro group, an amino group, a thiol group, a formyl group, a halo $C_1$-$C_4$ alkyl group, a $C_1$-$C_4$ alkoxy group, a linear or branched hydroxy $C_1$-$C_4$ alkyl group, a linear or branched $C_1$-$C_4$ alkyl group, a $C_2$-$C_4$ alkenyl group, a $C_2$-$C_4$ alkynyl group, a $C_3$-$C_{10}$ cycloalkyl group, a $C_2$-$C_9$ heterocycloalkyl group, a hydroxy$C_2$-$C_9$ heterocycloalkyl group, a linear or branched hydroxyl $C_1$-$C_4$ alkylcarbonyl group, $-NR^{10}R^{11}$, $-COR^{12}$, $-COOR^{12}$, or $-SO_2R^{13}$, q may be an integer from 0 to 5, wherein, when

A is piperazine or piperidine, q is not 0, and two or more $R^9$ may be connected or fused with

A to form a 7 to 12-membered bicycloalkyl group, heterobicycloalkyl group, spirocycloalkyl group, or spiroheterocycloalkyl group;

$R^{10}$ and $R^{11}$ may each independently be hydrogen, a hydroxy $C_1$-$C_4$ alkyl group, a halo $C_1$-$C_4$ alkyl group, a $C_1$-$C_4$ alkyl group, a $C_2$-$C_4$ alkenyl group, or a $C_2$-$C_4$ alkynyl group;

$R^{12}$ is hydrogen, a hydroxy group, a hydroxy $C_1$-$C_4$ alkyl group, a halo $C_1$-$C_4$ alkyl group, a $C_1$-$C_4$ alkyl group, a $C_2$-$C_4$ alkenyl group, a $C_2$-$C_4$ alkynyl group, a $C_3$-$C_{10}$ cycloalkyl group, or a $C_2$-$C_9$ heterocycloalkyl group;

$R^{13}$ may be hydroxy, a halo$C_1$-$C_4$ alkyl group, a $C_1$-$C_4$ alkyl group, a $C_2$-$C_4$ alkenyl group, a $C_2$-$C_4$ alkynyl group, a $C_3$-$C_{10}$ cycloalkyl group, a $C_2$-$C_9$ heterocycloalkyl group, aryl group, or $-NR_fR_g$, and $R_f$ and $R_g$ may each independently be hydrogen or a $C_1$-$C_4$ alkyl group.

According to an aspect of another embodiment, provided are methods of preparing the compounds.

According to an aspect of another embodiment, pharmaceutical compositions for preventing or treating cancer include the compounds or pharmaceutically acceptable salts thereof as an active ingredient.

According to an aspect of another embodiment, pharmaceutical compositions for preventing or treating FLT3 mediated disease include the compounds or pharmaceutically acceptable salts thereof as an active ingredient.

According to an aspect of another embodiment, pharmaceutical compositions for inhibiting FLT3 kinase activity include the compounds or pharmaceutically acceptable salts thereof and a pharmaceutically acceptable excipient.

According to an aspect of another embodiment, provided are methods of decreasing FLT3 activity of a subject in need by using the compounds.

According to an aspect of another embodiment, provided are methods of treating FLT3 mediated disease by using the compounds.

DETAILED DESCRIPTION

The present disclosure will be described in further detail.

Unless otherwise defined, all terms (including technical and scientific terms) used herein have the same meaning as commonly understood by one of ordinary skill in the art to which this disclosure belongs. Although example methods or materials are listed herein, other similar or equivalent ones are also within the scope of the present disclosure. Also, the numerical values set forth herein are considered to include the meaning of "about" unless explicitly stated. All publications disclosed as references herein are incorporated in their entirety by reference.

An aspect of the present disclosure provides a compound selected from a compound represented by Formula 1, and a stereoisomer, tautomer, solvate, or pharmaceutically acceptable salt thereof.

The residues indicated by $R^1$ to $R^{17}$, X, Y, Z, Z', A, B, Q, L, or $E^a$ to $E^d$ may be understood in the same ways as understood by one of ordinary skill in the art.

The term "halogen" includes fluorine, chlorine, bromine or iodine, unless otherwise indicated, and may be, for example, fluorine or chlorine, but is not limited thereto.

The term "alkyl" refers to a saturated monovalent hydrocarbon radical. The term "alkenyl" used herein refers to a monovalent hydrocarbon radical containing at least one carbon-carbon double bond, wherein each double bond may have an E- or Z-steric configuration. The term "alkynyl" used herein refers to a monovalent hydrocarbon radical containing at least one carbon-carbon triple bond. Such an alkyl group, an alkenyl group, and an alkynyl group may be linear, i.e., straight- or side-chained. As defined above, the number of carbon atoms in an alkyl group may be 1, 2, 3, 4, 5, or 6; or 1, 2, 3, or 4. Examples of alkyl include methyl, ethyl, propyl including n-propyl and iso-propyl, n-butyl, sec-butyl, butyl including iso-butyl and a tert-butyl, pentyl including n-pentyl, 1-methylbutyl, iso-pentyl, neo-pentyl, and tert-pentyl, hexyl including n-hexyl, 3,3-dimethylbutyl, and iso-hexyl. A double bond of an alkenyl group and a triple bond of an alkynyl group may each be in any position. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-enyl (=propagyl), but-2-enyl, but-3-enyl, hex-4-enyl, and hex-5-enyl. In a case where each of the compounds is sufficiently stable and suitable for a desirable use as, for example, a pharmaceutical substance, a substituted alkyl group, a substituted alkenyl group, and a substituted alkynyl group may be substituted at any position.

The term "cycloalkyl", unless otherwise stated, refers to a substituted or unsubstituted cyclic alkyl group, and an example of a single or multi-cyclic group is a mono- or bicycloaliphatic group. Examples of a cycloalkyl group include cyclopropyl, cyclobutyl, cyclopentyl, cyclohexyl, cyclohexenyl, cycloheptyl, cycloheptenyl, cyclooctyl, cyclooctenyl, 2, 5-cyclohexadienyl, bicyclo[2.2.2]octyl, adamant-1-yl, decahydronaphthyl group, oxo cyclohexyl, dioxo cyclohexyl, thio cyclohexyl, 2-oxo bicyclo[2.2.1]hept-1-yl, or any suitable isomer thereof without limitation.

The term "a bicycloalkyl group" used herein refers to, unless otherwise stated, a saturated carbocycle including two rings, and includes a fused carbocycle in which the two rings share two adjacent atoms as a part of the rings and a bridged carbocycle in which the two rings share two non-adjacent atoms as a part of the rings. For example, a 7 to 12-membered bicycloalkyl refers to a fused carbocycle or bridged carbocycle, each having a total of two rings constituted of 7 to 12 atoms.

The term "heterocycloalkyl" used herein, unless otherwise stated, refers to a substituted or unsubstituted mono cyclic or multicyclic alkyl containing at least one selected from O, N, and S, for example, 1 to 4 heteroatoms Examples of the mono heterocyclo alkyl group are piperazinyl, piperidinyl, piperazinyl-1-oxide, morpholinyl, thiamorpholinyl, pyrrolidinyl, imidazolidinyl, tetrahydrofuranyl, diazabicycloheptanyl, diazabicyclooctane, and diazaspirooctane, and groups similar thereto, but are not limited thereto.

The term "heterobicycloalkyl" used herein, unless otherwise stated, refers to a bicycloalkyl containing one or more hetero atom selected from O, N, and S, and includes a fused hetero bicycloalkyl group and a bridged hetero bicycloalkyl group. The term "bridged" used herein refers to a valence bond, single atom, or non-branched chain of atoms that connects two different parts inside a molecule. Also, a pair of tertiary or more carbon atoms linked through bridges is called "bridge heads." In other words, the carbon atoms that are simultaneously participating as a part of two or more rings are called bridge heads, and bonds connected to these bridge heads are called bridges. The term "bridged compound" used herein refers to a compound in which two or more rings share one or more pairs of carbon atoms.

Examples of a fused heterobicycloalkyl group include indole, quinoline, thiazolo[4, 5-b]-pyridine, quinoline, and the like, but are not limited thereto. Examples of bridged heterobicycloalkyl include 7 to 12 membered heterobicycloalkyls such as a diazabicyclo [2.2.1] heptane or a diazabicyclo [3.2.1] octane, but are not limited thereto.

The term "spiro" used herein refers to, unless defined otherwise, two rings which share one atom, wherein the two rings are not connected to each other by bridges. The term "spirocycloalkyl" used herein refers to, unless defined otherwise, a saturated carbocycle consisting of two rings, which share only one carbon atom as part of the rings. Examples of spirocycloalkyl include a 7 to 12 membered spirocycloalkyl group such as diazaspiro[2.5]octane, but are not limited thereto. The term "heterospirocycloalkyl" refers to, unless defined otherwise, a spirocycloalkyl containing at least one heteroatom selected from O, N, and S. The expression"spiro connection" used herein refers to a linker sharing one atom, unless defined otherwise.

The term "aryl" used herein, unless otherwise stated, refers to an aromatic group which may be substituted or unsubstituted, such as phenyl, biphenyl, naphthyl, toluyl, naphthalenyl, anthracenyl, or any suitable isomer thereof without limitation.

The term "heteroaryl" used herein, unless otherwise stated, refers to a monocyclic or bicyclic or higher aromatic group containing at least one heteroatom selected from O, N, and S, for example, from 1 to 4 heteroatoms. Examples of monocyclic heteroaryl are thiazolyl, oxazolyl, thiophenyl, furanyl, pyrrolyl, imidazolyl, isoxazolyl, pyrazolyl, triazolyl, thiadiazolyl, tetrazolyl, oxadiazolyl, pyridinyl, pyridazinyl, pyrimidinyl, pyrazinyl, and the like, but examples thereof are not limited thereto. Examples of bicyclic heteroaryl are indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, purinyl, furopyridinyl, and the like, but are not limited thereto.

The term "alkylene bridge" refers to, unless defined otherwise, a linear or branched bivalent hydrocarbon bridge that connects two different carbons having an identical ring structure, may consist of carbon and hydrogen, is not unsaturated, and may have, for example, 3 to 6 carbon atoms, and examples thereof are propylene, n-butylene, and the like. An alkylene bridge may link any two carbons in a ring structure. At least one of methylene in the alkylene bridge may be substituted with at least one selected from —O—, —S—, —S(O)—, —S(O)$_2$—, and —N(R')—, wherein R' may be hydrogen, a $C_1$-$C_6$ alkyl group, a $C_3$-$C_7$ cycloalkyl group, or aryl. In the present specification, the numerical range indicated by using the term "to" refers to a range including the numerical values described before and after the term as the lower limit and the upper limit, respectively.

In an example embodiment of an aspect of the present disclosure, $R^1$ in the compound of Formula 1 may be hydrogen, a $C_1$-$C_4$ alkoxy group or a hydroxy group.

In an embodiment, $R^1$ in the compound of Formula 1 may be hydrogen, a halogen, a hydroxy group, or a $C_1$-$C_4$ alkoxyl group.

In an embodiment, $R^2$ in the compound of Formula 1 may be hydrogen, a halogen, a $C_1$-$C_4$ alkyl group or a halo $C_{1-4}$ alkyl group.

In an embodiment, $R^3$ in the compound of Formula 1 may be hydrogen, a hydroxy group, or a $C_1$-$C_4$ alkyl group. In an embodiment, $R^3$ may be hydrogen.

In an embodiment, $R^4$ in the compound of Formula 1 may be hydrogen, a halogen, a hydroxy group, a cyano group, a nitro group, an amino group, halo$C_{1-4}$alkyl group, a $C_1$-$C_4$ alkoxy group, a hydroxy$C_1$-$C_4$ alkyl group, a $C_1$-$C_4$alkyl group, a $C_2$-$C_4$ alkenyl group, or a $C_2$-$C_4$ alkynyl group. In an embodiment, $R^4$ may be hydrogen, a halogen, a hydroxy group, a $C_1$-$C_4$alkoxy group, a hydroxy$C_1$-$C_4$alkyl group, or a $C_1$-$C_4$alkyl group.

In an embodiment, $R^5$ and $R^6$ in the compound of Formula 1 may each independently be hydrogen, a halogen, a hydroxy group, a cyano group, or a $C_1$-$C_4$ alkyl group. In an embodiment, $R^5$ and $R^6$ may each independently be hydrogen or hydroxy.

In an embodiment, $R^7$ in the compound of Formula 1 may be a $C_3$-$C_7$ cycloalkyl group. In an embodiment, $R^7$ may be cyclopropyl.

In an embodiment, Y in the compound of Formula 1 may be —(CH$_2$)$_m$—, —(CH$_2$)$_m$—O—(CH$_2$)$_n$—, or —(CH$_2$)$_m$—CO—(CH$_2$)$_n$—, wherein m and n may each independently be an integer from 0 to 2. In an embodiment, Y may be —(CH$_2$)$_m$— wherein m may be an integer selected from 1 and 2.

In an embodiment, Z in the compound of Formula 1 may be a compound represented by Formula 3.

Formula 3

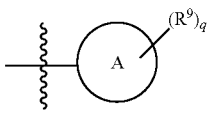

wherein, in Formula 3,

may be a $C_3$-$C_{10}$ cycloalkyl group or a $C_2$-$C_{11}$ heterocycloalkyl group;

$R^9$ may be halogen, a hydroxy group, a cyano group, a nitro group, an amino group, a thiol group, a formyl group, a halo $C_1$-$C_4$ alkyl group, a $C_1$-$C_4$ alkoxy group, a linear or branched hydroxy$C_1$-$C_4$ alkyl group, a linear or branched $C_1$-$C_4$ alkyl group, a $C_2$-$C_4$ alkenyl group, a $C_2$-$C_4$ alkynyl group, a $C_3$-$C_{10}$ cycloalkyl group, a $C_2$-$C_9$ heterocycloalkyl group, a hydroxy$C_2$-$C_9$ heterocycloalkyl group, a linear or branched hydroxy$C_{1-4}$ alkylcarbonyl group, —NR$^{10}$R$^{11}$, —COR$^{12}$, —COOR$^{12}$, or —SO$_2$R$^{13}$, q may each independently be an integer from 0 to 5, wherein, when

is piperazine or piperidine, q may not be 0, and 2 or more $R^9$ may be connected with each other or fused with

to form a 7 to 12-membered bicycloalkyl group;

$R^{10}$ and $R^{11}$ may each independently be hydrogen, a hydroxy $C_1$-$C_4$ alkyl group, a halo $C_1$-$C_4$ alkyl group, a $C_1$-$C_4$ alkyl group, a $C_2$-$C_4$ alkenyl group, or a $C_2$-$C_4$ alkynyl group;

$R^{12}$ is hydrogen, a hydroxy group, a hydroxy $C_{1-4}$ alkyl group, a halo $C_1$-$C_4$ alkyl group, a $C_1$-$C_4$ alkyl group, a $C_2$-$C_4$ alkenyl group, a $C_2$-$C_4$ alkynyl group, a $C_3$-$C_{10}$ cycloalkyl group, or a $C_2$-$C_9$ heterocycloalkyl group;

$R^{13}$ is hydroxy, a halo$C_1$-$C_4$ alkyl group, a $C_1$-$C_4$ alkyl group, a $C_2$-$C_4$ alkenyl group, a $C_2$-$C_4$ alkynyl group, a $C_3$-$C_{10}$ cycloalkyl group, a $C_2$-$C_9$ heterocycloalkyl group, aryl group, or —NR$_f$R$_g$, and R$_f$ and R$_g$ are each independently hydrogen or a $C_1$-$C_4$ alkyl group.

In an example of Formula 3,

may be a $C_3$-$C_6$ heterocycloalkyl including one or two heteroatoms selected from O, N, and S;

$R^9$ may each independently be hydrogen, a hydroxy group, a linear or branched hydroxy $C_1$-$C_4$ alkyl group, a linear or branched $C_1$-$C_4$ alkyl group, a $C_3$-$C_{10}$ cycloalkyl group, a $C_2$-$C_9$ heterocycloalkyl group, a hydroxy $C_2$-$C_9$ heterocycloalkyl group, —NR$^{10}$R$^{11}$ or —COR$^{12}$, $R^{10}$ and $R^{11}$ may be each independently hydrogen, a hydroxy $C_1$-$C_4$ alkyl group, or a $C_1$-$C_4$ alkyl group; and $R^{12}$ may be hydrogen, a hydroxy group, a hydroxy $C_1$-$C_4$ alkyl group, a halo $C_1$-$C_4$ alkyl group, or a $C_1$-$C_4$ alkyl group.

In an example embodiment, in the compound of Formula 1,

X is H or OH, wherein, when X is OH, the compound represented by Formula 1 may include a tautomeric structure represented by Formula 2:

Formula 2

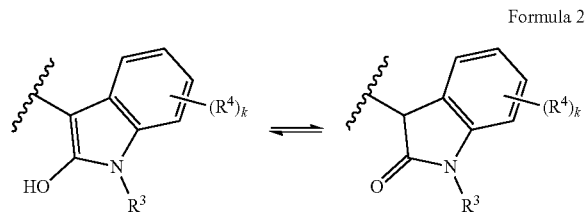

$R^3$, $R^4$, and k in Formula 2 are the same as described in connection with Formula 1.

In an example embodiment, in the compound of Formula 1,

X is H or OH, wherein, when X is OH, the compound represented by Formula 1 may include a tautomeric structure represented by Formula 2;

$R^1$ may be hydrogen, hydroxy, a $C_1$-$C_4$ alkoxy group, or a $C_1$-$C_4$ alkyl group;

$R^2$ may be hydrogen, a halogen, a $C_1$-$C_4$ alkyl group or a halo $C_1$-$C_4$ alkyl group;

$R^3$ may be hydrogen;

$R^4$ may be hydrogen, a halogen, a hydroxy group, a $C_1$-$C_4$ alkoxy group, a hydroxy $C_1$-$C_4$ alkyl group, or a $C_1$-$C_4$ alkyl group;

k may be an integer from 0 to 2;

$R^5$ and $R^6$ may each independently be hydrogen or a hydroxy group;

$R^7$ may be cyclopropyl;

Y may be —$(CH_2)_m$—, —$(CH_2)_m$—O—$(CH_2)_n$—, or —$(CH_2)_m$—CO—$(CH_2)_n$—;

m and n are each independently an integer from 0 to 2; and Z may be Formula 3;

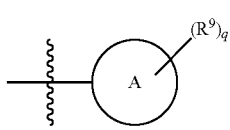

Formula 3 herein, in Formula 3,

may be a $C_3$-$C_6$ heterocycloalkyl including one or two heteroatoms selected from O, N, and S;

$R^9$ may each independently be hydroxy, a hydroxy $C_1$-$C_4$ alkyl group, a $C_1$-$C_4$ alkyl group, a $C_3$-$C_{10}$ cycloalkyl group, a $C_2$-$C_9$ heterocycloalkyl group, a hydroxy $C_2$-$C_9$ heterocycloalkyl group, —$NR^{10}R^{11}$, or —$COR^{12}$, $R^{10}$ and $R^{11}$ may be each independently hydrogen, a hydroxy $C_1$-$C_4$ alkyl group, or a $C_1$-$C_4$ alkyl group;

$R^{12}$ may be hydrogen, a hydroxy $C_1$-$C_4$ alkyl group, a halo $C_1$-$C_4$ alkyl group, or a $C_1$-$C_4$ alkyl group, and q may each independently be an integer from 0 to 3.

In an example of the compound represented by Formula 1, when

is piperazinyl or piperidinyl, q may not be 0.

In an example of the compound represented by Formula 1, Z may be any one selected from Formula 11 to Formula 13.

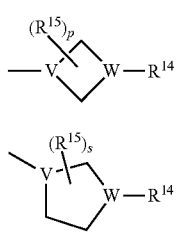

Formula 11

Formula 12

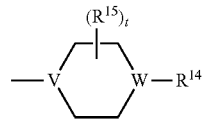

Formula 13 wherein, in Formulae 11 to 13,

V and W may each independently be N or a CH, provided that each of V and W is not CH at the same time.

$R^{14}$ may be hydrogen, a halogen, a linear or branched $C_1$-$C_4$ alkyl group, a linear or branched hydroxy $C_1$-$C_4$ alkyl, a hydroxy group, —$NR^{16}R^{17}$, a linear or branched hydroxy $C_1$-$C_4$ alkylcarbonyl group, a $C_2$-$C_9$ heterocycloalkyl group, a hydroxy $C_2$-$C_9$ heterocycloalkyl group, a linear or branched halo $C_1$-$C_4$ alkyl group, and a linear or branched $C_1$-$C_4$ alkoxy group, $R^{15}$ may each independently be a linear or branched $C_1$-$C_4$ alkyl group, a linear or branched hydroxy $C_1$-$C_4$ alkyl group, or halogen, $R^{14}$ and $R^{15}$ may be connected to each other, or $R^{14}$ or $R^{15}$ is fused with the cyclic compound represented by one of Formulae 11 to 13 to form a 7 to 12-membered bicycloalkyl group, heterobicycloalkyl group, spirocycloalkyl group, or spiroheterocycloalkyl group, $R^{16}$ and $R^{17}$ may each independently be hydrogen, a linear or branched $C_1$-$C_4$ alkyl group, or a linear or branched hydroxy $C_1$-$C_4$ alkyl group, p may be an integer from 0 to 4, and s and t may each independently be an integer from 0 to 5 when $R^{14}$ is hydrogen, and an integer from 0 to 4 when $R^{14}$ is not hydrogen.

Examples of the 7 to 12-membered bicycloalkyl formed by connecting $R^{14}$ and $R^{15}$ each other or fusing $R^{14}$ or $R^{15}$ with the cyclic compound represented by any one of Formulae 11 to 13 are diazabicycloheptanyl and diazabicyclooctanyl. In an embodiment, the 7 to 12-membered bicycloalkyl may be 2,5-diazabicyclo[2.2.1]heptanyl or 3,8-diazabicyclo[3.2.1]octanyl. Examples of the 7 to 12-membered spirocycloalkyl formed by connecting $R^{14}$ and $R^{15}$ each other or fusing $R^{14}$ or $R^{15}$ with the cyclic compound represented by any one of Formulae 11 to 13 may be a dazaspirooctayl group, for example, diazaspiro[2.5]octanyl.

In an example of the compound represented by Formula 1, $R^7$ may be a $C_3$-$C_7$ cycloalkyl and Z may be a substituted or unsubstituted $C_2$-$C_{11}$ heterocycloalkyl group. The $C_3$-$C_7$ cycloalkyl may be, for example, cyclopropyl, cyclobutyl, cyclopentyl, cyclohexyl, or cycloheptyl, but is not limited thereto. Z may be, for example, $C_3$-$C_7$ cycloalkyl unsubstituted or substituted with a halogen, hydroxy, cyano, nitro, amino, a halo $C_1$-$C_4$ alkyl, a $C_1$-$C_4$ alkoxy, a hydroxy $C_1$-$C_4$ alkyl, or a $C_1$-$C_4$ alkyl, but is not limited thereto. The $C_3$-$C_7$ cycloalkyl may be piperazinyl, piperidinyl, morpholinyl, thiomorpholinyl, pyrrolidinyl, imidazolidinyl, or tetrahydrofuranyl, and is not limited thereto.

In a compound according to an embodiment, $R^7$ may be cyclopropyl and Z may be a piperazinyl substituted with a $C_1$-$C_4$ alkyl group, for example, dimethylpiperazinyl. The compound according to an embodiment may have an improved pharmacokinetic profile and metabolic stability, such as microsomal stability.

In an embodiment, the compound of Formula 1 may be selected from a compound represented by Formula 14, and a stereoisomer, tautomer, solvate, or pharmaceutically acceptable salt thereof:

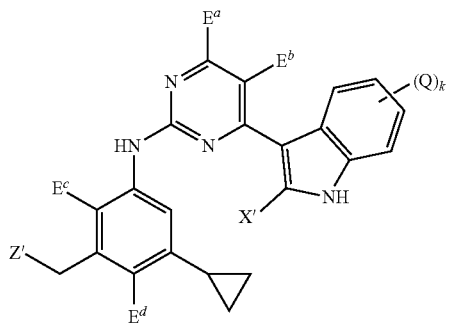

Formula 14 wherein, in Formula 14, $E^a$ may be hydrogen, a hydroxy group, or a $C_1$-$C_4$ alkoxy group;

$E^b$ may be hydrogen, a halogen, a $C_1$-$C_4$ alkyl group, or a $C_1$-$C_4$ fluoroalkyl group;

$E^c$ and $E^d$ may each independently be hydrogen or a hydroxy group;

X' may be hydrogen or a hydroxy group;

k may be an integer from 0 to 4;

Q may each independently be hydroxy, a halogen, a $C_1$-$C_4$ alkyl group, a hydroxy$C_1$-$C_4$ alkyl group, or a $C_1$-$C_4$ alkoxy group; and Z' may be a monovalent functional group represented by Formula 15.

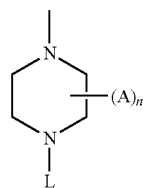

Formula 15 wherein, n in Formula 15 may be an integer from 1 to 8;

A may each independently be a functional group selected from hydroxy, a $C_1$-$C_4$ alkyl group, and a hydroxy$C_1$-$C_4$ alkyl group, wherein when n is two or more, two A may be linked to each other to form an alkylene bridge to form Z' being a 7 to 12-membered bridged heterobicycloalkyl ring, or two A may be spiro-connected to form a 7 to 12-membered spiroheterocycloalkyl ring;

L may be hydrogen, a $C_1$-$C_4$ alkyl, a hydroxy group, or a hydroxy$C_1$-$C_4$ alkyl group.

The compound selected from the compound of Formula 14, and a stereoisomer, tautomer, solvate, or pharmaceutically acceptable salt thereof may have improved properties compared to other compounds having similar chemical structures in aspects of a pharmacokinetic profile that is suitable for oral administration and a metabolic stability, such as microsomal stability.

The term "pharmacokinetic profile" used herein refers to the absorption, distribution, in vivo changes and excretion profile of a drug, from which the physiological and biochemical actions of drugs on the living body and their mechanism of action, that is, the response of the living body on the drugs may be identified.

The term "metabolic stability" such as microsomal stability used herein refers to the degree of stability of the metabolic organs after administration of the drug, and may affect pharmacokinetic parameters of the drug, such as clearance, half-life, and oral bioavailability. As an experiment to predict the degree of drug metabolism by the major organs in vitro, a metabolically active system, such as liver microsome or hepatocyte, may be used to measure metabolic stability.

In an embodiment, $E^b$ may be halogen, n may be an integer from 2 to 4, and A may be alkyl group, for example, methyl, ethyl, or propyl.

In an embodiment, $E^b$ may be halogen, n may be 2, and A may be methyl.

In an embodiment, Z' may be 3,5-dimethylpiperazine-1-yl.

In an embodiment, $E^b$ may be chlorine.

The compound selected from the compound of Formula 14, and a stereoisomer, tautomer, solvate, or pharmaceutically acceptable salt thereof may effectively control one or more kinases involved in intracellular signal transduction and intracellular complex biomechanisms. For example, the selected compound may act on receptor tyrosine kinase (RTK) to effectively control the intracellular delivery of extracellular stimuli. In an embodiment, the selected compound may effectively control fms-like tyrosine kinase 3 (FLT3) which is frequently abnormally overexpressed or mutated in patients with leukemia, and spleen tyrosine kinase (SYK) which acts on the signaling pathways of endothelial growth factor receptor (VEGFR), which are involved in controlling in the angiogenesis process, and other immunoreceptors such as B cell receptors and mast cells. The compound according to an embodiment effectively suppresses the mutation or overexpression of FLT3, and at the same time, the overexpression or overactivation of VEGFR, thereby blocking the supply of nutrition and oxygen to the tumor and suppressing SYK. Accordingly, the compound may be useful for the treatment of acute myelogenous leukemia (AML), which shows resistance to FLT3 inhibitors. The term "overall survival (OV)" used herein refers to the period of time from random allocation to death in clinical trials. FLT3-ITD positive acute myeloid leukemia (AML) is a disease with very low OV. SYK is overexpressed and activated in hematological malignant tumor, and highly activated SYK is usually found in FLT3-ITD-positive acute myeloid leukemia (AML), which has a very low OV. Therefore, as a target for the treatment of AML disease, SYK needs to be considered as an important factor together with FLT3.

The compound according to an embodiment shows an effective selective inhibitory activity against SYK as well as FLT3, thereby greatly improving the treatment efficiency for acute myeloid leukemia (AML) and increasing the OV time.

In an embodiment, L is hydrogen, a $C_1$-$C_4$ alkyl, a hydroxy group, or a hydroxy$C_1$-$C_4$ alkyl group;

$E^b$ is halogen, for example, chlorine, n is 2, and A is methyl;

The compound selected from the compound of Formula 14, and a stereoisomer, tautomer, solvate, or pharmaceutically acceptable salt thereof wherein Z' is 3,5-dimethylpiperazine-1-yl shows an excellent inhibitory activity against FLT3 and may effectively suppress the overexpression or overactivation of VEGFR and SYK. In addition, the compound may be effectively used for the prevention or treatment of cell proliferative diseases caused by abnormal activity of FLT3, VEGFR and SYK to enhance the tumor treatment efficacy. Therefore, the compound may be useful for the treatment of cancer or leukemia having resistance to FLT3 inhibitors of the related art, for example, AML.

In an embodiment, the compound of Formula 1 may be a compound selected from compounds listed in Table 1:

TABLE 1

| No. | Compound |
|---|---|
| 1 | 5-chloro-N-(3-cyclopropyl-5-(((3R,5S)-3,5-dimethylpiperazine-1-yl)methyl)phenyl)-4-(6-fluoro-1H-indole-3-yl)pyrimidine-2-amine |
| 2 | 5-chloro-4-(6-chloro-1H-indole-3-yl)-N-(3-cyclopropyl-5-(((3R,5S)-3,5-dimethylpiperazine-1-yl)methyl)phenyl)pyrimidine-2-amine |
| 3 | 2-((2R,6S)-4-(3-((5-chloro-4-(6-fluoro-1H-indole-3-yl)pyrimidine-2-yl)amino)-5-cyclopropylbenzyl)-2,6-dimethylpiperazine-1-yl)ethane-1-ol |
| 4 | 2-((2R,6S)-4-(3-((5-chloro-4-(1H-indole-3-yl)pyrimidine-2-yl)amino)-5-cyclopropylbenzyl)-2,6-dimethylpiperazine-1-yl)ethane-1-ol |
| 5 | 2-((2R,6S)-4-(3-((5-chloro-4-(6-methyl-1H-indole-3-yl)pyrimidine-2-yl)amino)-5-cyclopropylbenzyl)-2,6-dimethylpiperazine-1-yl)ethane-1-ol |
| 6 | (R)-5-chloro-N-(3-cyclopropyl-5-((3-methylpiperazine-1-yl)methyl)phenyl)-4-(1H-indole-3-yl)pyrimidine-2-amine |
| 7 | (R)-5-chloro-N-(3-cyclopropyl-5-((3-methylpiperazine-1-yl)methyl)phenyl)-4-(6-methyl-1H-indole-3-yl)pyrimidine-2-amine |
| 8 | 5-chloro-N-(3-cyclopropyl-5-(((3R,5S)-3,5-dimethylpiperazine-1-yl)methyl)phenyl)-4-(6-methyl-1H-indole-3-yl)pyrimidine-2-amine |
| 9 | 5-chloro-N-(3-cyclopropyl-5-(((3S,5R)-3-ethyl-5-methylpiperazine-1-yl)methyl)phenyl)-4-(6-methyl-1H-indole-3-yl)pyrimidine-2-amine |
| 10 | 5-chloro-N-(3-cyclopropyl-5-((3,5-dimethylpiperazine-1-yl)methyl)phenyl)-4-(6-methyl-1H-indole-3-yl)pyrimidine-2-amine |
| 11 | N-(3-cyclopropyl-5-(((3R,5S)-3,5-dimethylpiperazine-1-yl)methyl)phenyl)-4-(6-methyl-1H-indole-3-yl)pyrimidine-2-amine |
| 12 | N-(3-cyclopropyl-5-(((3R,5S)-3,5-dimethylpiperazine-1-yl)methyl)phenyl)-5-fluoro-4-(6-methyl-1H-indole-3-yl)pyrimidine-2-amine |
| 13 | N-(3-cyclopropyl-5-(((3R,5S)-3,5-dimethylpiperazine-1-yl)methyl)phenyl)-4-(1H-indole-3-yl)-5-methylpyrimidine-2-amine |
| 14 | N-(3-cyclopropyl-5-(((3R,5S)-3,5-dimethylpiperazine-1-yl)methyl)phenyl)-5-methyl-4-(6-methyl-1H-indole-3-yl)pyrimidine-2-amine |
| 15 | N-(3-cyclopropyl-5-(((3R,5S)-3,5-dimethylpiperazine-1-yl)methyl)phenyl)-4-(6-methyl-1H-indole-3-yl)-5-(trifluoromethyl)pyrimidine-2-amine |
| 16 | (3-(5-chloro-2-((3-cyclopropyl-5-(((3R,5S)-3,5-dimethylpiperazine-1-yl)methyl)phenyl)amino)pyrimidine-4-yl)-1H-indole-6-yl)methanol |
| 17 | 5-chloro-N-(3-cyclopropyl-5-(((3R,5S)-3,5-dimethylpiperazine-1-yl)methyl)phenyl)-4-(5-methoxy-6-methyl-1H-indole-3-yl)pyrimidine-2-amine |
| 18 | 3-(5-chloro-2-((3-cyclopropyl-5-(((3R,5S)-3,5-dimethylpiperazine-1-yl)methyl)phenyl)amino)pyrimidine-4-yl)-6-methyl-1H-indole-5-ol |
| 19 | 3-(5-chloro-2-((3-cyclopropyl-5-(((3R,5S)-3,5-dimethylpiperazine-1-yl)methyl)phenyl)amino)pyrimidine-4-yl)-6-methylindoline-2-one |
| 20 | 5-chloro-N-(3-cyclopropyl-5-(((3R,5S)-3,5-dimethylpiperazine-1-yl)methyl)phenyl)-4-methoxy-6-(6-methyl-1H-indole-3-yl)pyrimidine-2-amine |
| 21 | 5-chloro-2-((3-cyclopropyl-5-(((3R,5S)-3,5-dimethylpiperazine-1-yl)methyl)phenyl)amino)-6-(6-methyl-1H-indole-3-yl)pyrimidine-4-ol |
| 22 | 3-(5-chloro-2-((3-cyclopropyl-5-(((3R,5S)-3,5-dimethylpiperazine-1-yl)methyl)phenyl)amino)pyrimidine-4-yl)-6-methyl-1H-indole-7-ol |
| 23 | 2-((5-chloro-4-(6-methyl-1H-indole-3-yl)pyrimidine-2-yl)amino)-4-cyclopropyl-6-(((3R,5S)-3,5-dimethylpiperazine-1-yl)methyl)phenol |
| 24 | 4-((5-chloro-4-(6-methyl-1H-indole-3-yl)pyrimidine-2-yl)amino)-2-cyclopropyl-6-(((3R,5S)-3,5-dimethylpiperazine-1-yl)methyl)phenol |
| 25 | (R)-5-chloro-N-(3-cyclopropyl-5-((3,3,5-trimethylpiperazine-1-yl)methyl)phenyl)-4-(6-methyl-1H-indole-3-yl)pyrimidine-2-amine |
| 26 | ((2R,6R)-4-(3-((5-chloro-4-(6-methyl-1H-indole-3-yl)pyrimidine-2-yl)amino)-5-cyclopropylbenzyl)-6-methylpiperazine-2-yl)methanol |
| 27 | (R)-5-chloro-N-(3-cyclopropyl-5-((5-methyl-4,7-diazaspiro[2.5]octan-7-yl)methyl)phenyl)-4-(6-methyl-1H-indole-3-yl)pyrimidine-2-amine |
| 28 | 5-chloro-N-(3-cyclopropyl-5-(((3R,5R)-3,5-dimethylpiperazine-1-yl)methyl)phenyl)-4-(6-methyl-1H-indole-3-yl)pyrimidine-2-amine |

TABLE 1-continued

| No. | Compound |
|---|---|
| 29 | 5-chloro-N-(3-cyclopropyl-5-(((3S,5S)-3,5-dimethylpiperazine-1-yl)methyl)phenyl)-4-(6-methyl-1H-indole-3-yl)pyrimidine-2-amine |
| 30 | 5-chloro-N-(3-cyclopropyl-5-(((3R,5S)-3,4,5-trimethylpiperazine-1-yl)methyl)phenyl)-4-(6-methyl-1H-indole-3-yl)pyrimidine-2-amine |
| 31 | (2R,6S)-4-(3-((5-chloro-4-(6-methyl-1H-indole-3-yl)pyrimidine-2-yl)amino)-5-cyclopropylbenzyl)-2,6-dimethylpiperazine-1-ol |
| 32 | (2R,6S)-4-(3-cyclopropyl-5-((4-(6-methyl-1H-indole-3-yl)pyrimidine-2-yl)amino)benzyl)-2,6-dimethylpiperazine-1-ol |

The term "isomer" used herein refers to a compound having the same molecular formula and a different structure. The compounds of Formula 1 according to an aspect of the present disclosure may exist as various compounds having the isomer relationship in a three-dimensional aspect, and these isomers and mixtures are within the scope of the present disclosure. In one or more embodiment, the compounds of Formula 1 according to an aspect of the present disclosure may exist as a stereoisomer or structural isomer, for example, a tautomer.

The term "stereoisomer" used herein refers to a compound that has the same molecular formula and the same connection order of atoms and is different in stereoscopic or optical aspects. That is, a stereoisomer refers to a compound having the same chemical composition but being different in the three-dimensional arrangement aspect, that is, being different in the arrangement of atoms or groups. The stereoisomer includes geometric isomers, enantiomeric isomers, and partial stereoisomers.

The term "geometrical isomer" used herein refers to the type of a stereoisomer depending on the direction of a functional group in a molecule, and may be called a cis-trans isomer. Generally, these isomers contain non-rotatable double bonds and the substituents of compounds containing double bonds may be in an E form or a Z form. For example, when the compound contains a 2-substituted cycloalkyl group, the compound may have the cis-trans form. When the compound of Formula 1 contains a bridged ring, the compound may exist as an exo or endo isomer.

The term "chiral" used herein refers to a molecule having a non-overlapping enantiomeric partner, and the term "achiral" used herein refers to a molecule having an overlapping enantiomeric partner. The term "enantiomer" used herein refers to the case where two molecules having optical activity are mirror-symmetrical. That is, the enantiomer indicates an isomer that does not overlap an original molecule, and does not have any of the symmetry elements including the symmetry plane and the symmetry center, and has the stereoscopic center (chiral center). The term "diastereomer" used herein refers to the case in which molecules having two or more chiral centers are not enantiomers but stereoisomers. Since the compounds of Formula 1 according to an aspect of the present disclosure may have chiral centers or asymmetric carbon centers (absent carbons), the compounds may exist as the enantiomer (R or S isomer), racemates, diastereoisomers, or a mixture thereof, and all of these isomers and mixtures are included within the scope of the present disclosure. The optically active (R)- and (S)-isomers may be decomposed by using techniques of the related art or chiral synthon or chiral reagents.

The term "constitutional isomers" used herein refers to isomers having the same molecular formula but different connection orders of atoms, and may include tautomer. The term "tautomers" used herein refers to constitutional isomers having different energy structures that are interchanged through low energy barriers. For example, a photon tautomer (also a proton tautomer) includes interconversion through the transfer of photons, such as keto-enol and imine-enamine isomerization. Valence tautomers include interconversions by the rearrangement of some electrons in the bound electrons. The compound of Formula 1 according to an aspect, and the stereoisomer or tautomer thereof may exist in the form of solvate. The term "solvate" may include a molecular complex including the compound and at least one pharmaceutically acceptable solvent molecule, e.g., ethanol or water. A complex, in which the solvent molecule is water, is also referred to as "hydrate".

The compound of Formula 1 according to an aspect, and the stereoisomer, tautomer, and solvate thereof may exist in the form of a pharmaceutically acceptable salt. The term "pharmaceutically acceptable salt" used herein refers to a salt that is low in toxicity to humans and does not adversely affect the biological activity and physicochemical properties of the parent compound. Pharmaceutically acceptable salts include pharmaceutically acceptable acid addition salts and pharmaceutically acceptable base addition salts of the compound represented by Formula 1, which would be understood by those skilled in the art.

The pharmaceutically acceptable salts may be prepared by a conventional method. For example, the compound of Formula 1 may be dissolved in a solvent, which is capable of being mixed with water, e.g., methanol, ethanol, acetone, 1,4-dioxane, and then, a free acid or a free base may be added thereto for crystallization to thereby prepare a pharmaceutically acceptable salt.

Another aspect of the present disclosure provides a method of preparing the compounds.

In accordance with another aspect of the present disclosure, provided is a method of preparing the compound of Formula 1 including reacting a compound of Formula 6 with a compound of Formula 7:

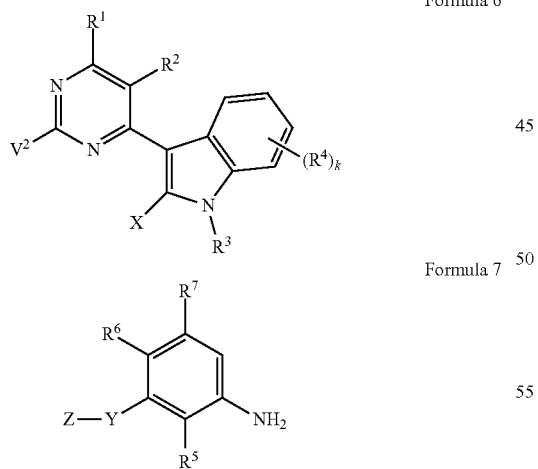

Formula 6

Formula 7 wherein $R^1$, $R^2$, $R^3$, $R^4$, $R^5$, $R^6$, $R^7$, X, Y, Z, and k in Formulae 6 and 7 may be the same as described in connection with Formulae 1 and 2, and $V^2$ may be halogen.

An organic base, e.g., triethylamine, diisopropylethylamine, pyridine, and the like; an inorganic base, e.g., sodium carbonate, potassium carbonate, hydrogenated sodium, and the like; an organic acid, e.g., trifluoroacetic acid, toluenesulfonic acid, and the like; or an inorganic acid, e.g., hydrochloric acid, sulfuric acid, phosphoric acid, and the like, may or may not be added to a reaction solution when performing the reaction. A solvent used in the reaction may be any solvent that does not inhibit the reaction, for example, a polar aprotic solvent such as dimethylsulfoxide, N, N-dimethylformamide, acetonitrile, or tetrahydrofuran (THF); a polar protic solvent such as methanol, ethanol, 2-propanol, or 2-butanol; or a nonpolar aprotic solvent such as toluene or 1,4-dioxane. A reaction temperature may be in a range of 0° C. to 150° C., for example, from room temperature to about 100° C.

In an example embodiment, the compound of Formula 1 may be prepared as shown in Reaction Scheme 1:

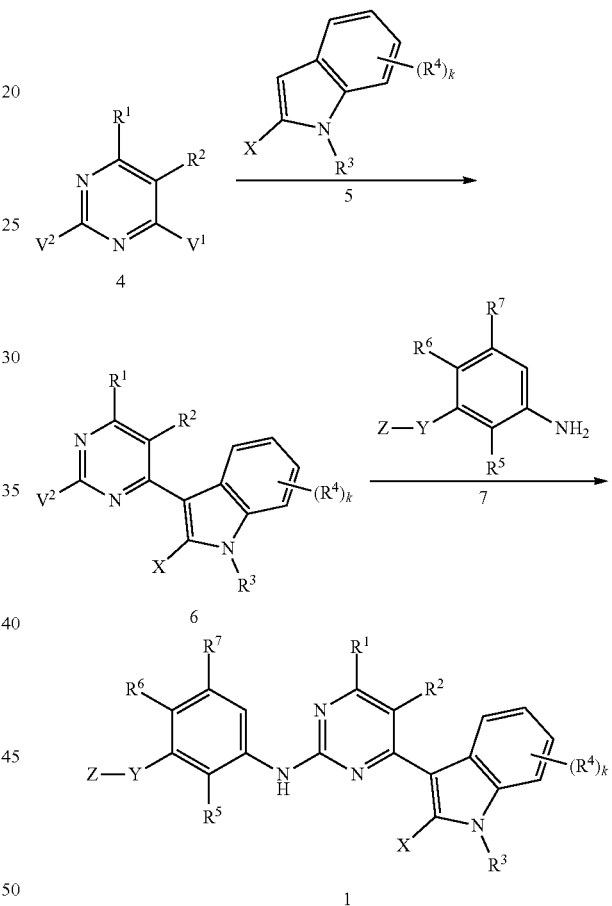

Reaction Scheme 1

The compounds of Formulae 4 and 5 may be prepared by using conventional knowledge in the field of organic chemistry.

wherein, in Reaction Scheme 1, $R^1$, $R^2$, $R^3$, $R^4$, $R^5$, $R^6$, $R^7$, X, Y, Z, and k may respectively be defined the same as those of Formulae 1 and 2, and $V^1$ and $V^2$ may each independently be halogen.

In preparing the compound of Formula 6 by reacting the compound of Formula 4 with the compound of Formula 5, the reaction may be performed by adding an organometallic compound. For example, the organometallic compound may be an alkyl magnesium compound or an alkyl lithium compound.

A solvent used in the reacting may be any solvent that does not inhibit the reaction, for example, a polar aprotic solvent such as dimethylsulfoxide, N, N-dimethylformamide, acetonitrile, or THF; or a nonpolar aprotic solvent such as toluene or 1,4-dioxane. A reaction temperature may be in a range of 0° C. to 100° C., for example, from 0° C. to 60° C.

In preparing the compound of Formula 7, when Y is —$(CH_2)_m$—, m may be an integer from 1 to 2, when Y is —$(CH_2)_m$—O—$(CH_2)_n$—, m may be 0 and n may each independently be an integer from 0 to 2, when Y is —$(CH_2)_m$—CO—$(CH_2)_n$—, each of m and n may be 0, and the compound is prepared based on the common knowledge of the corresponding organochemical field as explained in connection with Preparation Schemes 1 to 3.

Preparation Scheme 1 in a case where Y is —$(CH_2)_m$—:

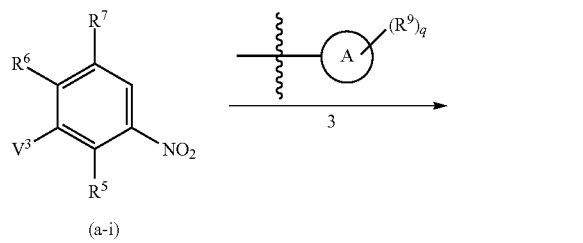

In Preparation Scheme 1, $R^5$, $R^6$, $R^7$, $R^9$,

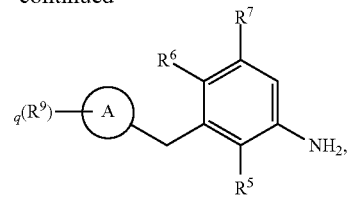

and q are the same as described in connection with Formulae 1 and 3, and $V^3$ may be halogen and L may be Cl, Br, I, OMs, OTs, or the like.

Preparation Scheme 2 in a case where Y is —$(CH_2)_m$—O—$(CH_2)_n$—:

-continued

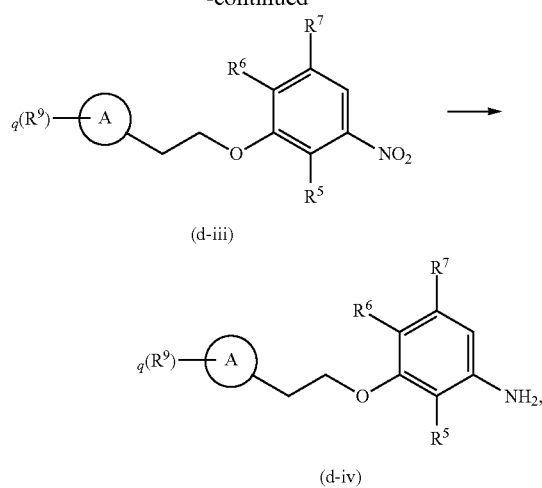

(d-iii)

(d-iv)

n = 2

In Preparation Scheme 2, $R^5$, $R^6$, $R^7$, $R^9$,

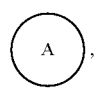

and q are the same as described in connection with Formulae 1 and 3, and L may be Cl, Br, I, OMs, OTs, or the like.

Preparation Scheme 3 in a case where Y is —(CH$_2$)$_m$—CO—(CH$_2$)$_n$—:

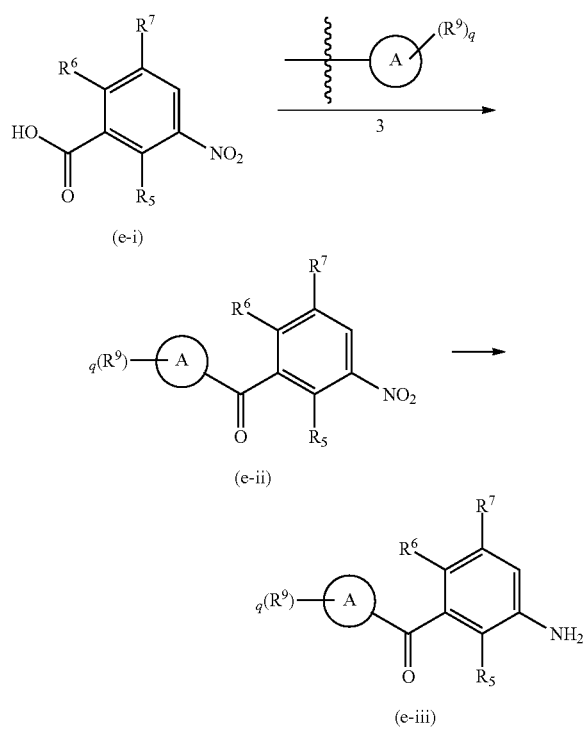

(e-i)

(e-ii)

(e-iii)

In Preparation Scheme 3, $R^5$, $R^6$, $R^7$, $R^9$,

and q are the same as described in connection with Formulae 1 and 3.

Another aspect of the present disclosure provides, a method of preparing a compound represented by Formula 1a, the method including a compound represented by Formula 10 and a compound represented by Formula 3:

Formula 10

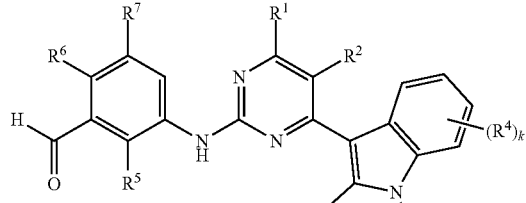

Formula 3

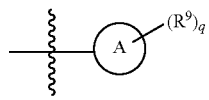

Formula 1a

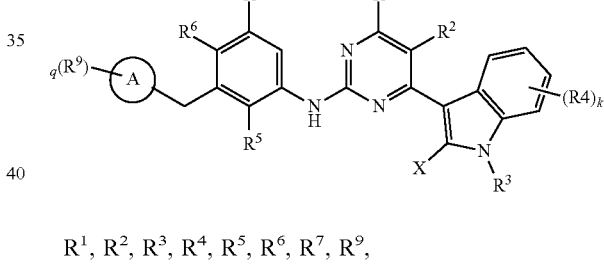

$R^1$, $R^2$, $R^3$, $R^4$, $R^5$, $R^6$, $R^7$, $R^9$,

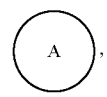

X, k, and q in Formulae 10, 3, and 1a are the same as described in connection with Formulae 1, 2, and 3.

The reaction may be carried out by adding or not adding, to a reaction solution, a reducing agent, such as sodium borohydride, sodium cyano borohydride, sodium triacetoxyborohydride and the like; an organic base, such as triethylamine, diisopropylethylamine, and pyridine; an inorganic base, such as sodium carbonate, potassium carbonate, and hydrogenated sodium; an organic acid, such as trifluoroacetic acid, toluenesulfonic acid and the like; or an inorganic acid, such as hydrochloric acid, sulfuric acid, and phosphoric acid. The solvent used in the reaction may be any solvent that does not inhibit the reaction, and examples of the solvent are a polar aprotic solvent, such as dichloromethane, 1,2-dichloroethane, dimethyl sulfoxide, N, N-dimethylformamide, acetonitrile or tetrahydrofuran; a polar protic solvent, such as methanol, ethanol, 2-propanol, or 2-butanol;

and non-polar aprotic solvents, such as toluene or 1,4-dioxane. A reaction temperature may be in a range of 0° C. to 150° C., for example, room temperature.

The compound of Formula 10 may be prepared using conventional knowledge in the field of organic chemistry.

In an embodiment, the compound represented by Formula 1a may be prepared by using the method illustrated in Reaction Scheme 2.

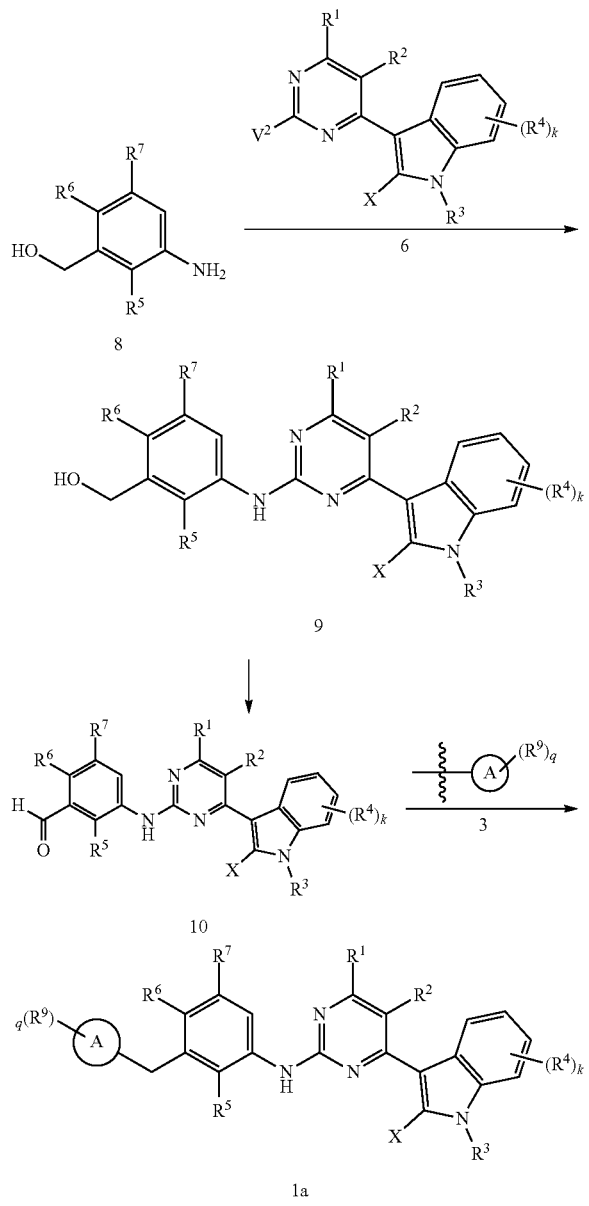

In Reaction Scheme 2, $R^1$, $R^2$, $R^3$, $R^4$, $R^5$, $R^6$, $R^7$, $R^9$,

X, k, and q are the same as described in connection with Formulae 1, 2, and 3, and $V^2$ is halogen.

To prepare a compound of Formula 10 from a compound of Formula 9, the compound of Formula 9 is oxidized by using an oxidant, such as $MnO_2$ and then, washed with an organic solvent, such as methylene chloride, followed by concentrating and purifying the obtained organic layer.

To prepare the compound of Formula 9 by reacting a compound of Formula 8 with a compound of Formula 6, the solvent used in the reaction may be any solvent that does not inhibit the reaction. For example, the reaction may be carried out by adding or not adding, to a reaction solution, an organic base such as triethylamine, diisopropylethylamine, and pyridine; an inorganic base such as sodium carbonate, potassium carbonate, and hydrogenated sodium; an organic acid such as trifluoroacetic acid, toluenesulfonic acid and the like; or an inorganic acids such as hydrochloric acid, sulfuric acid, and phosphoric acid, and a base or acid equivalent may be 0.1 to 5 equivalents based on one equivalent of Compound 1 of Formula B. The solvent used in the reaction may be a polar aprotic solvent, such as dimethylsulfoxide, N, N-dimethyl formamide, acetonitrile, tetrahydrofuran, or the like; a polar protic solvent, such as methanol, ethanol, 2-propanol, or 2-butanol; or a non-polar aprotic solvents, such as toluene or 1,4-dioxane. A reaction temperature may be in a range of 0° C. to 150° C., for example, from 50° C. to about 100° C.

Although the method of the preparing Formula 1 has been described by way of specific examples, specific reaction conditions, such as an amount of a reaction solvent, a base, and a reactant to be used, are not limited to those described in the present specification, and may not be construed as limiting the scope of the present disclosure.

Another aspect of the present disclosure provides a pharmaceutical composition for the prevention or treatment of cancer, the composition including the compound or a pharmaceutically acceptable salt thereof as the active ingredient.

The cancer may include leukemia, such as acute myelogenous leukemia (AML), chronic myelogenous leukemia (CML), acute lymphocytic leukemia (ALL), chronic lymphocytic leukemia (CLL), acute promyelocytic leukemia (APL), hairy cell leukemia, chronic neutrophilic leukemia (CNL), or the like.

In one embodiment, the cancer may be leukemia.

In an embodiment, the leukemia may include AML, ALL, or CML.

Another aspect of the present disclosure provides a pharmaceutical composition for the prevention or treatment of FLT3-mediated disease, the composition including the compound or a pharmaceutically acceptable salt thereof as the active ingredient.

Another aspect of the present disclosure provides a pharmaceutical composition for inhibiting FLT3 kinase activity, the pharmaceutical composition including the compound according to an aspect or a pharmaceutically acceptable salt thereof and a pharmacologically acceptable excipient.

In an example embodiment, the pharmaceutical composition may include a pharmaceutically acceptable excipient or additive. The pharmaceutical composition of the present disclosure may be formulated according to a conventional method and may be formulated into various oral dosage forms such as a tablet, a pill, powder, a capsule, syrup, emulsion, and microemulsion; or parenteral dosage forms such as intramuscular, intravenous or subcutaneous administration.

When the pharmaceutical composition of the present disclosure is prepared in a form of an oral formulation, examples of a carrier or additive to be used include a diluent, a disintegrant, a binder, a lubricant, a surfactant, a suspension, and an emulsifier. When the pharmaceutical composition of the present disclosure is prepared in a form of an injection, examples of a carrier or additive may include water, saline solution, aqueous glucose solution, pseudosaccharide solution, alcohol, glycol, ether (e.g., polyethylene glycol 400), oil, fatty acid, fatty acid ester, glyceride, a surfactant, a suspension, and an emulsifier. Such formulation methods are well known to those of ordinary skill in the pharmaceutical art.

In an embodiment, as the active ingredient included in the pharmaceutical composition, the compound of Formula 1 may be administered in an effective amount for the treatment or prevention to a subject or patient. The compound of Formula 1 may be administered orally or parenterally, according to purpose. When the compound is administered orally, the active ingredient may be administered in an amount in a range of 0.01 milligrams (mg) to 1,000 mg, for example, 0.01 mg to 500 mg, for example, 0.1 mg to 300 mg, for example, 0.1 to 100 mg, per kilogram (kg) of body weight per day. When the compound is administered parenterally, the active ingredient may be administered from one to several times in an amount in a range of 0.01 mg to 100 mg, for example, 0.1 mg to 50 mg, per kg of body weight per day. The composition may be administered once for all or in several divided doses. The dose for a subject or patient should be determined in light of the patient's weight, age, sex, health condition, diet, time of administration, method of administration, severity of disease, etc. It is to be understood that the dose may be appropriately adjusted by a practitioner. The dose is not intended to limit the scope of the disclosure in any aspects.

Another aspect of the present disclosure provides a method of preventing or treating cancer by using the compound according to the aspect. In an embodiment, the method may include administering the compound selected from the compound of Formula 1 according to an aspect and the stereoisomer, tautomer, solvate, or pharmaceutically acceptable salt thereof to a subject. The subject may be a patient. Another aspect of the present disclosure provides a method of inhibiting FLT3 activity of a target subject by using the compound according to the aspect.

Another aspect of the present disclosure provides a method of treating FLT3-mediated disease by using the compound according to the aspect.

Details of the method of preventing or treating may be the same as described above with reference to the pharmaceutical composition according to an aspect of the present disclosure.

In an embodiment, the dosage, the number of administrations, or method of administration of the compound used for the treatment may vary depending on the subject to be treated, severity of disease or condition, the speed of administration, and judgment of a prescribing doctor. The dosage for a human with a body weight of 70 kg may be in the range of 0.1 to 2,000 mg per day, for example, 1 to 1,000 mg or 10 to 2,000 mg. The number of administrations may be administered once to several times, for example, 1 to 4 times or according to on/off schedules, and the administration method may be administered an oral or parenteral route. In one or more embodiments, the dosage may be less than the range described above. In one or more embodiments, the dosage may be greater than the range described above without causing harmful side effects. In the latter case, the dosage may be dispensed in several small portions throughout a day. Physicians having ordinary skill in the relevant art may determine and prescribe the dosage of a compound according to purpose. For example, physicians may use the dosage of the compound according to embodiments of the present disclosure at a level being lower than that required to achieve the target therapeutic effect, and then gradually increase the dosage until the target effect is obtained.

In one embodiment, according to the method, as an active ingredient, the compound according to one aspect of the present disclosure may be used alone, or in combination with one or more other pharmaceutical drugs known to treat cancer, tumor or leukemia, or pharmaceutical carriers. In one embodiment, the compound selected from the compound represented by Formula 1, and the stereoisomer, tautomer, solvate, or pharmaceutically acceptable salt thereof may be administered together with other inhibitors of FLT3 kinase activity or other agents of various mechanisms that increase the efficacy of FLT3 kinase activity inhibition or exhibit synergistic action to decrease the FLT3 activity or enhance the therapeutic effect of the FLT3 mediated disease.

The term "treatment" used herein includes treatment, improvement, amelioration, or management of disease. The term "treating" or "treatment" used herein refers to inhibiting disease, for example, inhibiting a disease, condition or disorder, preventing further development of pathology and/or symptoms, improving disease, or reversing pathology and/or symptoms, for example, reducing the severity of the disease, in a subject who experiences or shows a pathology or symptom of a disease, condition or disorder.

The term "preventing" or "prevention" used herein refers to prevention of a disease, for example, prevention of a disease, condition, or disorder in a subject that may be predisposed to have the disease, condition, or disorder but have not yet experienced or exhibited pathology or a symptom of the disease.

The term "subject" or "patient" used herein refers to any animal, including mammals, for example, mice, rats, other rodents, rabbits, dogs, cats, pigs, cows, sheep, horses, or primates and humans.

The terms "having," "may have," "including," or "may include" may refer to the presence of a feature (e.g., a component such as a number, component, etc.), and does not exclude the presence of additional features.

Hereinafter, the present disclosure will be described in more detail with reference to the following Examples and Experimental Examples. However, Examples and Experimental Examples are intended to help understand the present disclosure, and the scope of the present disclosure is not limited thereto in any sense.

Example 1: 5-chloro-N-(3-cyclopropyl-5-(((3R, 5S)-3,5-dimethylpiperazine-1-yl)methyl)phenyl)-4-(6-fluoro-1H-indole-3-yl)pyrimidine-2-amine Process 1) Preparation of 3-bromo-5-nitrobenzoic acid

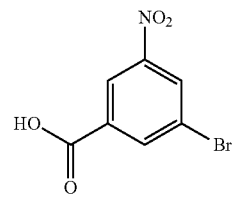

500 g (2991.86 mmol)) of 3-nitrobenzoic acid was dissolved in 1.4 L of concentrated (conc.) sulfuric acid ($H_2SO_4$), and the temperature was raised to 60° C. 652 g (3590.23 mmol) of N-bromosuccinimide was added thereto three times for 1 hour, and the result was stirred at a temperature of 60° C. for 2 hours. Once the reaction was complete, ice was added to the reaction mixture. The resulting solid was obtained through filtration and dried in an oven at a temperature of 40° C. for 16 hours to obtain 730 g of the target compound in the yield of 99.2%.

$^1$H-NMR (300 MHz, DMSO-$d_6$): δ 8.59 (s, 1H), 8.51 (s, 1H), 8.38 (s, 1H).

Process 2) Preparation of (3-bromo-5-nitrophenyl)methanol

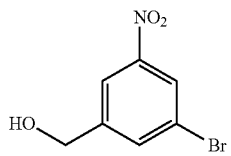 [SMILES: O=[N+]([O-])c1cc(Br)cc(CO)c1]

200 g (812.94 mmol) of 3-bromo-5-nitrobenzoic acid prepared in Process 1) was dissolved in 1.25 L of tetrahydrofuran (THF), and the temperature was decreased to 0° C. 1.6 L (3251.76 mmol) of borane-dimethylsulfide (2.0 M in THF) was slowly added dropwise thereto for 1.5 hours. The mixture was stirred at room temperature for 16 hours, and then stirred under reflux at a temperature of 80° C. for 1 hour. Once the reaction was complete, the resultant was cooled to room temperature, and saturated sodium hydrogen carbonate was added dropwise thereto. An extraction process was performed thereon three times using ethyl acetate, and an organic layer was washed with saline water, dried using anhydrous sodium sulfate, and concentrated under reduced pressure. The obtained residue was purified using column chromatography (chloromethylene:methanol=10:1 (v/v)), and the resulting solution was concentrated under reduced pressure and then crystallized by using hexane to thereby obtain 180 g of a target compound in the yield of 95.4%.

$^1$H-NMR (300 MHz, DMSO-$d_6$): δ 8.23 (s, 1H), 8.17 (s, 1H), 7.96 (s, 1H), 4.63 (s, 2H).

Process 3) Preparation of (3-cyclopropyl-5-nitrophenyl)methanol

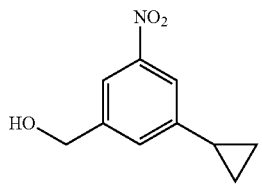

100 g (431.00 mmol) of (3-bromo-5-nitrophenyl)methanol prepared according to Process 2) and 111 g (1293.00 mmol) of cyclopropylborate, 9.7 g (43.10 mmol) of Pd(OAc)$_2$, 274.5 g (1293.00 mmol) of potassium phosphate, and 33.92 g (129.30 mmol) of triphenylphosphine were dissolved in a mixed solvent of toluene and $H_2O$ (2:1, 1.35 L) and then purged with nitrogen for 5 minutes. The reaction mixture was sealed, and the temperature was raised to 100° C., followed by stirring under reflux for 20 hours. Once the reaction was complete, the mixed solution was cooled to room temperature, and the mixed solution was filtered using a celite filter. The celite layer was washed with ethyl acetate. An organic layer was extracted three times from the mixed solution, which underwent the filtration, and the organic layer was washed with saline water, dried using anhydrous sodium sulfate, and concentrated under reduced pressure. The obtained residue was purified using column chromatography (ethyl acetate:hexane=1:5 (v/v)), and the resulting solution was concentrated under reduced pressure to thereby obtain 62 g of a target compound in the yield of 74.5%.

$^1$H-NMR (300 MHz, DMSO-$d_6$): δ 8.07 (s, 1H), 7.71 (s, 1H), 7.25 (s, 1H), 4.70 (s, 2H), 1.90 (m, 1H), 1.01 (m, 2H), 0.71 (m, 2H).

Process 4) Preparation of (3R, 5S)-1-(3-cyclopropyl-5-nitrobenzyl)-3,5-dimethylpiperazine

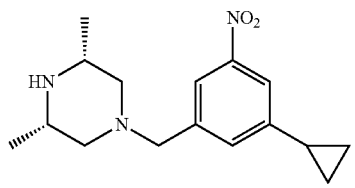 [SMILES: C[C@@H]1CN(Cc2cc(C3CC3)cc([N+](=O)[O-])c2)C[C@H](C)N1]

2 g (10.35 mmol) of (3-cyclopropyl-5-nitrophenyl)methanol prepared according to Process 3) was dissolved in a mixed solvent including tetrahydrofuran and water (1:1, 66 mL), and the temperature was decreased to -0°. Sodium hydroxide (NaOH; 829 mg, 20.70 mmol) and 3.95 g (20.70 mmol) of p-Toluenesulfonyl chloride were added thereto. After stirring for 1 hour at a temperature of 0° C., water was added dropwise thereto at room temperature. An extraction process was performed thereon three times using ethyl acetate, and an organic layer was washed with saline water, dried using anhydrous sodium sulfate, and concentrated under reduced pressure. The obtained residue was dissolved in 11 mL of N,N-dimethylformamide, and 796 mg (5.76 mmol) of potassium carbonate ($K_2CO_3$) and 394 mg (3.45 mmol) of (2R, 6S)-2,6-dimethylpiperazine were added thereto and the resultant mixture was stirred under reflux at a temperature of 100° for 1 hour. Once the reaction was complete, the mixed solution was cooled to room temperature, and ethyl acetate and water was added dropwise thereto. An organic layer was extracted therefrom, and the organic layer was washed with saline water, dried using anhydrous sodium sulfate, and concentrated under reduced pressure. The obtained residue was purified using MPLC (chloroform:methanol=10:1 (v/v)), and the resulting solution was concentrated under reduced pressure to thereby obtain 645 mg of a target compound in the yield of 77%.

$^1$H-NMR (300 MHz, CDCl$_3$): δ 7.95 (s, 1H), 7.76 (s, 1H), 7.37 (s, 1H), 3.53 (m, 2H), 3.44 (t, 4H), 2.39 (t, 4H), 1.45 (m, 9H), 1.04 (m, 2H), 0.76 (m, 2H).

Process 5) Preparation of 3-cyclopropyl-5-(((3R, 5S)-3,5-dimethylpiperazine-1-yl)methyl)aniline

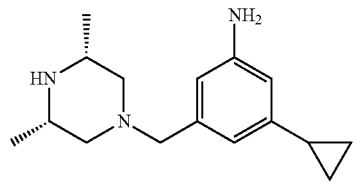

11 mL of 50% ethanol was added to 622 mg (11.14 mmol) of Fe powder, and 0.1 mL (0.89 mmol) of concentrated hydrochloric acid (conc.HCl) was slowly added dropwise thereto, and the resultant mixture was stirred under reflux at a temperature of 110° C. for 1.5 hours. (3R, 5S)-1-(3-cyclopropyl-5-nitrobenzyl)-3,5-dimethylpiperazine (645 mg, 2.23 mmol) prepared according to Process 4) was added to the activated Fe mixture, and the resultant mixture was stirred under reflux at a temperature of 110° C. for 1 hour. Once the reaction was complete, a filtration process was performed thereon using a celite filter. A mixed solution of chloroform and methanol and saturated sodium hydrogen carbonate solution were added dropwise to the filtrate. An organic layer was separated from the mixture solution, washed with saline water, dried using anhydrous sodium sulfate, and concentrated under reduced pressure to thereby obtain 518 mg of a target compound in the yield of 90%.

Process 6) Preparation of 5-chloro-N-(3-cyclopropyl-5-(((3R, 5S)-3,5-dimethylpiperazine-1-yl)methyl)phenyl)-4-(6-fluoro-1H-indole-3-yl)pyrimidine-2-amine

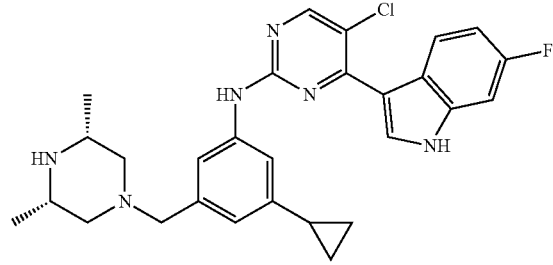 [SMILES: C[C@@H]1CN(Cc2cc(Nc3ncc(Cl)c(-c4c[nH]c5cc(F)ccc45)n3)cc(C3CC3)c2)C[C@H](C)N1]

46 mg (0.17 mmol) of 3-cyclopropyl-5-(((3R, 5S)-3,5-dimethylpiperazine-1-yl)methyl)aniline prepared according to Process 5) and 50 mg (0.17 mmol) of 3-(2,5-dichloropyrimidine-4-yl)-6-fluoro-1H-indole, of which preparation method is disclosed in WO2013014448, were dissolved in 2 mL of 2-butanol, and 34 mg (0.17 mmol) of p-toluene sulfonic acid (p-TsOH) was added thereto. This reaction mixture was stirred under reflux at a temperature of 120° C. for 21 hours. Once the reaction was complete, the mixture was cooled to room temperature, and a saturated sodium hydrogen carbonate solution was added dropwise thereto, followed by an extraction process using chloroform twice. The extracted organic layer was washed with saline water, dried using anhydrous sodium sulfate, and concentrated under reduced pressure. The obtained residue was purified using column chromatography (chloroform:methanol=9:1 (v/v)), and the resulting solution was concentrated under reduced pressure to thereby obtain 11 mg of a target compound in the yield of 12%.

MS (ESI$^+$, m/z): 505 [M+H]$^+$ $^1$H-NMR (300 MHz, DMSO-d$_6$): δ 11.94 (bs, 1H), 9.50 (s, 1H), 8.60 (m, 1H), 8.50 (s, 1H), 8.44 (s, 1H), 7.43 (s, 1H), 7.36 (s, 1H), 7.29 (m, 1H), 6.96 (m, 1H), 6.63 (s, 1H), 2.70 (m, 4H), 1.85 (m, 1H), 1.44 (m, 2), 0.92 (m, 8H), 0.60 (m, 2H).

Example 2: 5-chloro-4-(6-chloro-1H-indole-3-yl)-N-(3-cyclopropyl-5-(((3R, 5S)-3,5-dimethylpiperazine-1-yl)methyl)phenyl)pyrimidine-2-amine

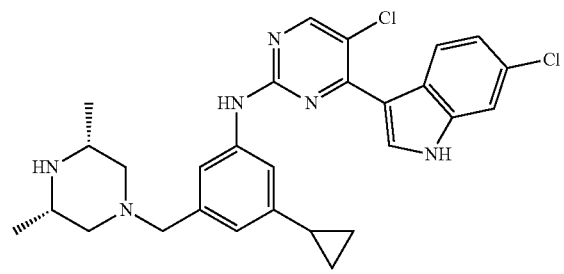 [SMILES: C[C@@H]1CN(Cc2cc(Nc3ncc(Cl)c(-c4c[nH]c5cc(Cl)ccc45)n3)cc(C3CC3)c2)C[C@H](C)N1]

97 mg of a target compound was obtained in the yield of 69% in substantially the same manner as in Process 6) of Example 1, except that 89 mg (0.30 mmol) of 6-chloro-3-(2,5-dichloropyrimidine-4-yl)-1H-indole was used instead of 3-(2,5-dichloropyrimidine-4-yl)-6-fluoro-1H-indole in Process 6) of Example 1.

MS (ESI$^+$, m/z): 521 [M+H]$^+$ $^1$H-NMR (300 MHz, DMSO-d$_6$): δ 12.01 (s, 1H), 9.54 (s, 1H), 8.58 (d, 1H), 8.54 (s, 1H), 8.46 (s, 1H), 7.55 (m, 1H), 7.46 (m, 1H), 7.36 (s, 1H), 7.11 (m, 1H), 6.65 (s, 1H), 3.37 (s, 2H), 2.85 (m, 2H), 2.71 (d, 2H), 1.84 (m, 1H), 1.60 (m, 2H), 0.95 (d, 7H), 0.89 (m, 2H), 0.61 (m, 2H).

Example 3: 2-((2R, 6S)-4-(3-((5-chloro-4-(6-fluoro-1H-indole-3-yl)pyrimidine-2-yl)amino)-5-cyclopropylbenzyl)-2,6-dimethylpiperazine-1-yl)ethane-1-ol

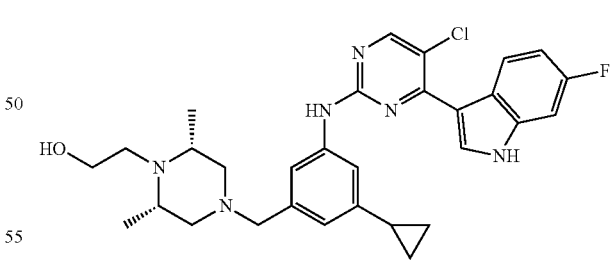

38 mg of a target compound was obtained in the yield of 63% in substantially the same manner as in Process 6) of Example 1, except that 32 mg (0.11 mmol) of 2-((2R, 6S)-4-(3-amino-5-cyclopropylbenzyl)-2,6-dimethylpiperazine-1-yl)ethane-1-ol was used instead of 3-cyclopropyl-5-(((3R, 5S)-3,5-dimethylpiperazine-1-yl)methyl)aniline.

MS (ESI$^+$, m/z): 549 [M+H]$^+$ $^1$H-NMR (300 MHz, DMSO-d$_6$): δ 11.94 (bs, 1H), 9.51 (s, 1H), 8.59 (m, 1H), 8.54 (m, 1H), 8.49 (s, 1H), 7.42 (s, 3H), 7.36 (s, 1H), 7.27 (d, 1H), 6.96 (t, 1H), 6.62 (s, 1H), 4.35 (m, 1H), 3.39 (m, 4H), 3.27 (m, 2H), 2.48 (m, 4H), 1.82 (m, 1H), 1.59 (m, 2H), 0.89 (m, 8H), 0.57 (m, 2H).

Example 4: 2-((2R, 6S)-4-(3-((5-chloro-4-(1H-indole-3-yl)pyrimidine-2-yl)amino)-5-cyclopropylbenzyl)-2,6-dimethylpiperazine-1-yl)ethane-1-ol

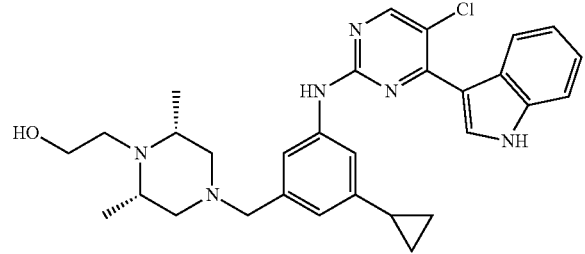 [SMILES: C[C@@H]1CN(Cc2cc(Nc3ncc(Cl)c(-c4c[nH]c5ccccc45)n3)cc(C3CC3)c2)C[C@H](C)N1CCO]

18 mg of a target compound was obtained in the yield of 31% in substantially the same manner as in Process 6) of Example 1, except that 32 mg (0.11 mmol) of 2-((2R, 6S)-4-(3-amino-5-cyclopropylbenzyl)-2,6-dimethylpiperazine-1-yl)ethane-1-ol was used instead of 3-cyclopropyl-5-(((3R, 5S)-3,5-dimethylpiperazine-1-yl)methyl)aniline, and 31 mg (0.11 mmol) of 3-(2,5-dichloropyrimidine-4-yl)-1H-indole was used instead of 3-(2,5-dichloropyrimidine-4-yl)-6-fluoro-1H-indole.

MS (ESI+, m/z): 531 [M+H]$^+$ $^1$H-NMR (300 MHz, DMSO-d$_6$): δ 11.90 (bs, 1H), 9.48 (s, 1H), 8.57 (d, 1H), 8.54 (m, 1H), 8.47 (s, 1H), 7.49 (m, 3H), 7.23 (m, 1H), 7.18 (m, 1H), 6.61 (s, 1H), 4.35 (m, 1H), 3.39 (m, 4H), 3.27 (m, 2H), 2.48 (m, 4H), 1.82 (m, 1H), 1.59 (m, 2H), 0.89 (m, 8H), 0.59 (m, 2H).

Example 5: 2-((2R, 6S)-4-(3-((5-chloro-4-(6-methyl-1H-indole-3-yl)pyrimidine-2-yl)amino)-5-cyclopropylbenzyl)-2,6-dimethylpiperazine-1-yl)ethane-1-ol

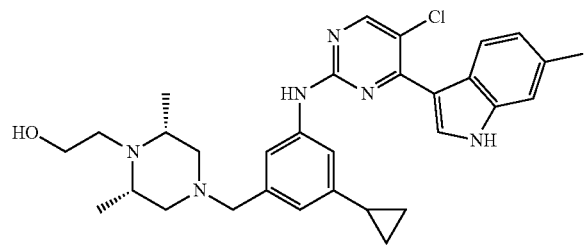 [SMILES: Cc1ccc2c(-c3nc(Nc4cc(CN5C[C@@H](C)N(CCO)[C@@H](C)C5)cc(C5CC5)c4)ncc3Cl)c[nH]c2c1]

28 mg of a target compound was obtained in the yield of 47% in substantially the same manner as Process 6) of Example 1, except that 32 mg (0.11 mmol) of 2-((2R, 6S)-4-(3-amino-5-cyclopropylbenzyl)-2,6-dimethylpiperazine-1-yl)ethane-1-ol was used instead of 3-cyclopropyl-5-(((3R, 5S)-3,5-dimethylpiperazine-1-yl)methyl)aniline, and 31 mg (0.11 mmol) of 3-(2,5-dichloropyrimidine-4-yl)-6-methyl-1H-indole was used instead of 3-(2,5-dichloropyrimidine-4-yl)-6-fluoro-1H-indole.

MS (ESI+, m/z): 545 [M+H]$^+$ $^1$H-NMR (300 MHz, DMSO-d$_6$): δ 11.76 (bs, 1H), 9.45 (s, 1H), 8.45 (m, 3H), 7.43 (d, 1H), 7.25 (s, 1H), 6.94 (d, 1H), 6.61 (s, 1H), 4.35 (m, 1H), 3.39 (m, 4H), 3.27 (m, 2H), 2.48 (m, 4H), 2.40 (s, 3H), 1.82 (m, 1H), 1.59 (m, 2H), 0.89 (m, 8H), 0.59 (m, 2H).

Example 6: (R)-5-chloro-N-(3-cyclopropyl-5-((3-methylpiperazine-1-yl)methyl)phenyl)-4-(1H-indole-3-yl)pyrimidine-2-amine

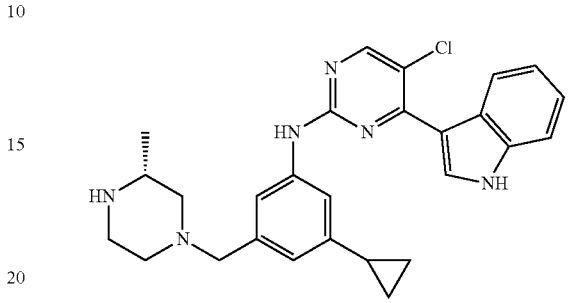

32 mg of a target compound was obtained in the yield of 17% in substantially the same manner as Process 6) of Example 1, except that 100 mg (0.41 mmol) of (R)-3-cyclopropyl-5-((3-methylpiperazine-1-yl)methyl)aniline was used instead of 3-cyclopropyl-5-(((3R, 5S)-3,5-dimethylpiperazine-1-yl)methyl)aniline, and 108 mg (0.41 mmol) of 3-(2,5-dichloropyrimidine-4-yl)-1H-indole was used instead of 3-(2,5-dichloropyrimidine-4-yl)-6-fluoro-1H-indole.

MS (ESI+, m/z): 473 [M+H]$^+$ $^1$H-NMR (300 MHz, DMSO-d$_6$): δ 11.93 (s, 1H), 9.52 (s, 1H), 8.58 (d, 1H), 8.50 (d, 1H), 8.46 (s, 1H), 7.54 (m, 3H), 7.22 (t, 1H), 7.15 (m, 1H), 6.65 (s, 1H), 3.77 (m, 1H), 3.45 (m, 2H), 3.21 (m, 2H), 2.95 (m, 1H), 2.82 (m, 2H), 2.28 (s, 3H), 2.20 (m, 1H), 2.01 (m, 1H), 1.84 (m, 1H), 0.93 (m, 2H), 0.63 (m, 2H).

Example 7: (R)-5-chloro-N-(3-cyclopropyl-5-((3-methylpiperazine-1-yl)methyl)phenyl)-4-(6-methyl-1H-indole-3-yl)pyrimidine-2-amine

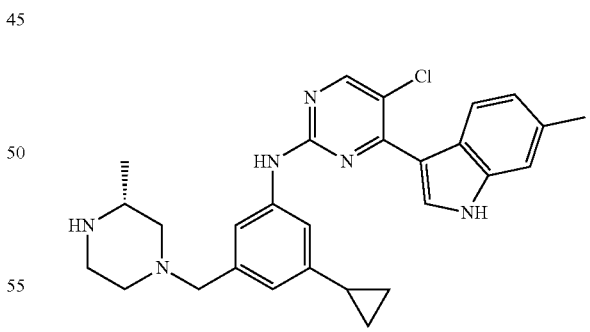

39 mg of a target compound was obtained in the yield of 38% in substantially the same manner as in Process 6) of Example 1, except that 53 mg (0.21 mmol) of (R)-3-cyclopropyl-5-((3-methylpiperazine-1-yl)methyl)aniline was used instead of 3-cyclopropyl-5-(((3R, 5S)-3,5-dimethylpiperazine-1-yl)methyl)aniline, and 66 mg (0.24 mmol) of 3-(2,5-dichloropyrimidine-4-yl)-6-methyl-1H-indole was used instead of 3-(2,5-dichloropyrimidine-4-yl)-6-fluoro-1H-indole.

MS (ESI+, m/z): 487 [M+H]+

¹H-NMR (300 MHz, DMSO-d₆): δ 11.77 (bs, 1H), 9.47 (s, 1H), 8.47 (m, 3H), 7.50 (s, 1H), 7.39 (s, 1H), 7.28 (s, 1H), 6.93 (d, 1H), 6.64 (s, 1H), 3.39 (s, 2H), 2.94 (m, 1H), 2.77 (m, 2H), 2.42 (s, 3H), 2.00 (m, 5H), 1.04 (m, 4H), 0.92 (m, 2H), 0.62 (m, 2H).

Example 8: 5-chloro-N-(3-cyclopropyl-5-(((3R, 5S)-3,5-dimethylpiperazine-1-yl)methyl)phenyl)-4-(6-methyl-1H-indol-3-yl)pyrimidine-2-amine

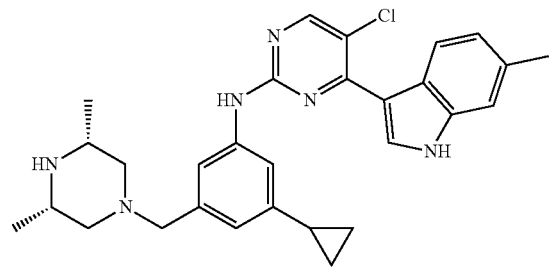

30 mg of a target compound was obtained in the yield of 7% in substantially the same manner as in Process 6) of Example 1, except that 222 mg (0.80 mmol) of 3-(2,5-dichloropyrimidine-4-yl)-6-methyl-1H-indole was used instead of 3-(2,5-dichloropyrimidine-4-yl)-6-fluoro-1H-indole in Process 6) of Example 1.

MS (ESI+, m/z): 501 [M+H]+

¹H-NMR (300 MHz, DMSO-d₆): δ 11.76 (bs, 1H), 9.45 (s, 1H), 8.47 (m, 3H), 7.46 (s, 1H), 7.39 (s, 1H), 7.27 (s, 1H), 6.96 (d, 1H), 6.63 (s, 1H), 2.69 (m, 2H), 2.60 (m, 2H), 2.42 (s, 3H), 1.84 (m, 1H), 1.45 (t, 2H), 0.91 (m, 8H), 0.62 (m, 2H).

Example 9: 5-chloro-N-(3-cyclopropyl-5-(((3S, 5R)-3-ethyl-5-methylpiperazine-1-yl)methyl)phenyl)-4-(6-methyl-1H-indol-3-yl)pyrimidine-2-amine

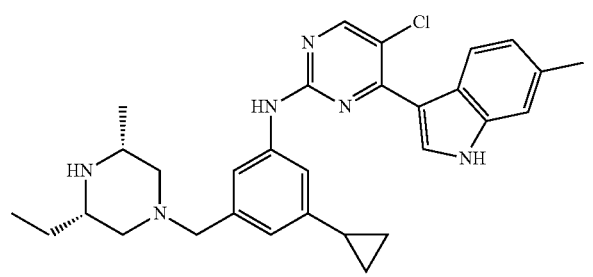 [SMILES: CC[C@H]1CN(Cc2cc(Nc3ncc(Cl)c(-c4c[nH]c5cc(C)ccc45)n3)cc(C3CC3)c2)C[C@@H](C)N1]

30 mg of a target compound was obtained in the yield of 29% in substantially the same manner as in Process 6) of Example 1, except that 55 mg (0.20 mmol) of 3-cyclopropyl-5-(((3S, 5R)-3-ethyl-5-methylpiperazine-1-yl)methyl)aniline was used instead of 3-cyclopropyl-5-(((3R, 5S)-3,5-dimethylpiperazine-1-yl)methyl)aniline, and 61 mg (0.22 mmol) of 3-(2,5-dichloropyrimidine-4-yl)-6-methyl-1H-indole was used instead of 3-(2,5-dichloropyrimidine-4-yl)-6-fluoro-1H-indole.

MS (ESI+, m/z): 515 [M+H]+

¹H-NMR (300 MHz, DMSO-d₆): δ 11.77 (bs, 1H), 9.45 (s, 1H), 8.47 (m, 3H), 7.46 (s, 1H), 7.39 (s, 1H), 7.27 (s, 1H), 6.96 (d, 1H), 6.63 (s, 1H), 3.36 (m, 2H), 2.70 (m, 4H), 2.42 (s, 3H), 1.85 (m, 1H), 1.50 (m, 2H), 0.93 (m, 11H), 0.61 (m, 2H).

Example 10: 5-chloro-N-(3-cyclopropyl-5-((3,5-dimethylpiperazine-1-yl)methyl)phenyl)-4-(6-methyl-1H-indol-3-yl)pyrimidine-2-amine

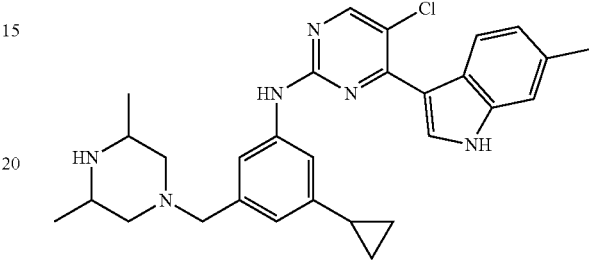

100 mg of a target compound was obtained in the yield of 52% in substantially the same manner as in Process 6) of Example 1, except that 100 mg (0.36 mmol) of 3-cyclopropyl-5-((3,5-dimethylpiperazine-1-yl)methyl)aniline was used instead of 3-cyclopropyl-5-(((3R, 5S)-3,5-dimethylpiperazine-1-yl)methyl)aniline, and 150 mg (0.54 mmol) of 3-(2,5-dichloropyrimidine-4-yl)-6-methyl-1H-indole was used instead of 3-(2,5-dichloropyrimidine-4-yl)-6-fluoro-1H-indole.

MS (ESI+, m/z): 501 [M+H]+

¹H-NMR (300 MHz, DMSO-d₆): δ 11.77 (s, 1H), 9.46 (s, 1H), 8.45 (m, 3H), 7.43 (d, 2H), 7.30 (s, 1H), 6.75 (d, 1H), 6.64 (s, 1H), 2.82 (m, 2H), 2.72 (d, 2H), 2.42 (s, 3H), 1.83 (m, 1H), 1.47 (t, 1H), 0.88 (s, 8H), 0.64 (m, 2H).

Example 11: N-(3-cyclopropyl-5-(((3R,5S)-3,5-dimethylpiperazine-1-yl)methyl)phenyl)-4-(6-methyl-1H-indol-3-yl)pyrimidine-2-amine

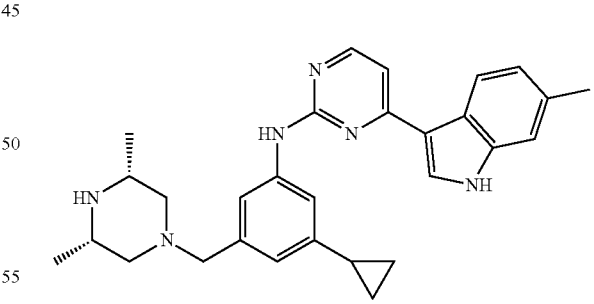

409 mg of a target compound was obtained in the yield of 31% in substantially the same manner as in Process 6) of Example 1, except that 700 mg (2.80 mmol) of 3-(2-chloropyrimidine-4-yl)-6-methyl-1H-indole was used instead of 3-(2,5-dichloropyrimidine-4-yl)-6-fluoro-1H-indole.

MS (ESI+, m/z): 467 [M+H]+

¹H-NMR (300 MHz, DMSO-d₆): δ 11.63 (bs, 1H), 9.20 (s, 1H), 8.44 (d, 1H), 8.28 (d, 1H), 8.19 (m, 1H), 7.51 (s, 1H), 7.44 (s, 1H), 7.22 (m, 2H), 6.96 (d, 1H), 6.59 (s, 1H), 4.20 (m, 1H), 3.15 (s, 3H), 2.71 (m, 2H), 2.65 (m, 3H), 2.40 (s, 3H), 1.85 (m, 1H), 1.48 (m, 2H), 0.93 (m, 2H), 0.90 (m, 6H), 0.62 (m, 2H).

Example 12: N-(3-cyclopropyl-5-(((3R, 5S)-3,5-dimethylpiperazine-1-yl)methyl)phenyl)-5-fluoro-4-(6-methyl-1H-indole-3-yl)pyrimidine-2-amine

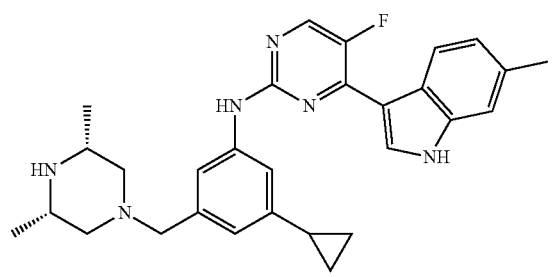

101 mg of a target compound was obtained in the yield of 77% in substantially the same manner as in Process 6) of Example 1, except that 78 mg (0.30 mmol) of 3-(2-chloro-5-fluoropyrimidine-4-yl)-6-methyl-1H-indole was used instead of 3-(2,5-dichloropyrimidine-4-yl)-6-fluoro-1H-indole.

MS (ESI⁺, m/z): 485 [M+H]⁺

¹H-NMR (300 MHz, DMSO-d₆): δ 11.83 (s, 1H), 9.36 (s, 1H), 8.60 (d, 1H), 8.40 (d, 1H), 8.10 (s, 1H), 7.48 (s, 1H), 7.40 (s, 1H), 7.29 (s, 1H), 7.00 (d, 1H), 6.62 (s, 1H), 3.42 (s, 2H), 2.98 (m, 2H), 2.79 (d, 2H), 2.43 (s, 3H), 1.87 (m, 1H), 1.70 (m, 2H), 1.08 (d, 7H), 0.96 (m, 2H), 0.67 (m, 2H).

Example 13: N-(3-cyclopropyl-5-(((3R, 5S)-3,5-dimethylpiperazine-1-yl)methyl)phenyl)-4-(1H-indole-3-yl)-5-methylpyrimidine-2-amine

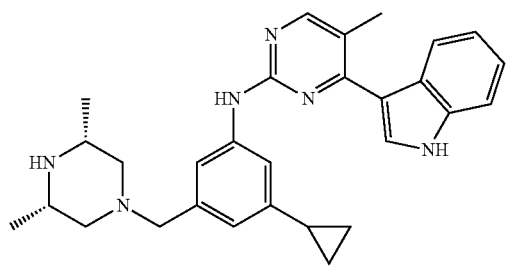 [SMILES: Cc1cnc(Nc2cc(CN3C[C@@H](C)N[C@@H](C)C3)cc(C3CC3)c2)nc1-c1c[nH]c2ccccc12]

99 mg of a target compound was obtained in the yield of 79% in substantially the same manner as in Process 6) of Example 1, except that 73 mg (0.30 mmol) of 3-(2-chloro-5-methylpyrimidine-4-yl)-1H-indole was used instead of 3-(2,5-dichloropyrimidine-4-yl)-6-fluoro-1H-indole.

MS (ESI+, m/z): 467 [M+H]⁺

¹H-NMR (300 MHz, DMSO-d₆): δ 11.74 (s, 1H), 9.15 (s, 1H), 8.58 (d, 1H), 8.27 (s, 1H), 8.00 (d, 1H), 7.55 (m, 3H), 7.20 (t, 1H), 7.12 (m, 1H), 6.56 (s, 1H), 3.37 (s, 2H), 2.86 (m, 2H), 2.70 (d, 2H), 2.37 (s, 3H), 1.75 (m, 1H), 1.57 (m, 2H), 0.95 (d, 7H), 0.91 (m, 2H), 0.60 (m, 2H).

Example 14: N-(3-cyclopropyl-5-(((3R, 5S)-3,5-dimethylpiperazine-1-yl)methyl)phenyl)-5-methyl-4-(6-methyl-1H-indole-3-yl)pyrimidine-2-amine

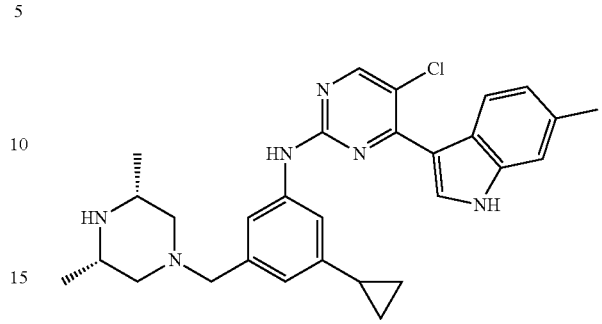

135 mg of a target compound was obtained in the yield of 73% in substantially the same manner as in Process 6) of Example 1, except that 150 mg (0.58 mmol) of 3-(2-chloro-5-methylpyrimidine-4-yl)-6-methyl-1H-indole was used instead of 3-(2,5-dichloropyrimidine-4-yl)-6-fluoro-1H-indole.

¹H-NMR (300 MHz, DMSO-d₆): δ 11.64 (s, 1H), 9.15 (s, 1H), 8.44 (d, 1H), 8.25 (s, 1H), 7.92 (d, 1H), 7.60 (s, 1H), 7.45 (s, 1H), 7.26 (s, 1H), 7.12 (s, 1H), 6.93 (d, 1H), 6.58 (s, 1H), 3.46 (s, 2H), 2.83 (d, 2H), 2.43 (s, 3H), 2.36 (s, 3H), 1.94 (t, 2H), 1.91 (m, 1H), 1.05 (t, 1H), 0.89 (m, 2H), 0.61 (t, 2H).

Example 15: N-(3-cyclopropyl-5-(((3R, 5S)-3,5-dimethylpiperazine-1-yl)methyl)phenyl)-4-(6-methyl-1H-indole-3-yl)-5-(trifluoromethyl)pyrimidine-2-amine

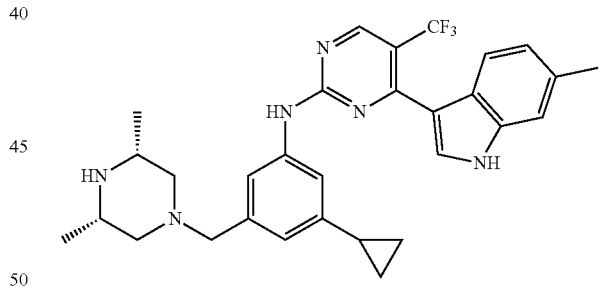

289 mg of a target compound was obtained in the yield of 28% in substantially the same manner as in Process 6) of Example 1, except that 600 mg (1.92 mmol) of 3-(2-chloro-5-(trifluoromethyl)pyrimidine-4-yl)-6-methyl-1H-indole was used instead of 3-(2,5-dichloropyrimidine-4-yl)-6-fluoro-1H-indole.

MS (ESI+, m/z): 535 [M+H]⁺

¹H-NMR (300 MHz, DMSO-d₆): δ 11.63 (bs, 1H), 9.87 (s, 1H), 8.69 (s, 1H), 8.28 (m, 1H), 7.77 (s, 1H), 7.49 (s, 1H), 7.39 (s, 1H), 7.26 (s, 1H), 6.93 (d, 1H), 6.66 (s, 1H), 4.20 (m, 1H), 3.15 (s, 3H), 2.58 (m, 3H), 2.55 (m, 3H), 2.40 (s, 3H), 1.85 (m, 1H), 1.40 (m, 2H), 0.89 (m, 8H), 0.57 (m, 2H).

Example 16: (3-(5-chloro-2-((3-cyclopropyl-5-(((3R, 5S)-3,5-dimethylpiperazine-1-yl)methyl)phenyl)amino)pyrimidine-4-yl)-1H-indole-6-yl)methanol Process 1) Preparation of (3-(5-chloro-2-((3-cyclopropyl-5-(((3R, 5S)-3,5-dimethylpiperazine-1-yl)methyl)phenyl)amino)pyrimidine-4-yl)-1-tosyl-1H-indole-6-yl)methanol

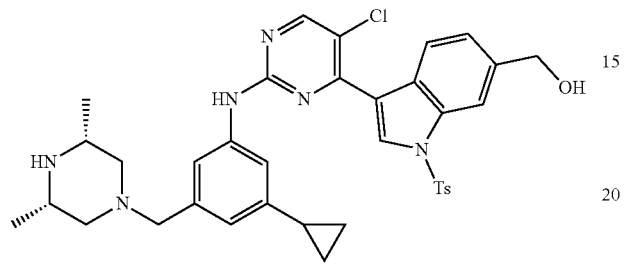

30 mg of a target compound was obtained in the yield of 46% in substantially the same manner as in Process 6) of Example 1, except that 51 mg (0.11 mmol) of (3-(2,5-dichloropyrimidine-4-yl)-1-tosyl-1H-indole-6-yl)methanol was used instead of 3-(2,5-dichloropyrimidine-4-yl)-6-fluoro-1H-indole.

$^1$H-NMR (300 MHz, DMSO-d$_6$): δ 9.70 (s, 1H), 8.62 (s, 1H), 8.58 (s, 1H), 8.29-8.03 (m, 2H), 7.53-7.09 (m, 4H), 6.33 (s, 1H), 5.39 (brs, 1H), 4.65 (s, 2H), 2.73 (m, 2H), 2.61 (d, 2H), 2.33 (s, 3H), 1.80 (m, 1H), 1.49 (t, 1H), 0.88 (m, 10H), 0.55 (m, 2H).

Process 2) Preparation of (3-(5-chloro-2-((3-cyclopropyl-5-(((3R, 5S)-3,5-dimethylpiperazine-1-yl)methyl)phenyl)amino)pyrimidine-4-yl)-1H-indole-6-yl)methanol

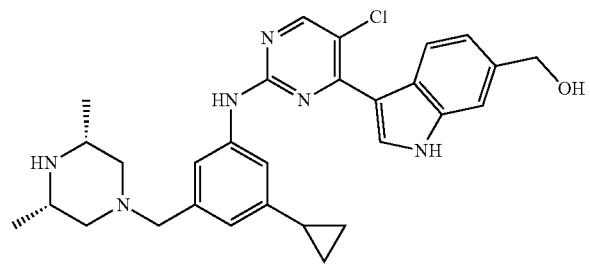 [SMILES: C[C@@H]1CN(Cc2cc(Nc3ncc(Cl)c(-c4c[nH]c5cc(CO)ccc45)n3)cc(C3CC3)c2)C[C@H](C)N1]

18 mg (0.03 mmol) of (3-(5-chloro-2-((3-cyclopropyl-5-(((3R, 5S)-3,5-dimethylpiperazine-1-yl)methyl)phenyl)amino)pyrimidine-4-yl)-1-tosyl-1H-indole-6-yl)methanol prepared according to Process 1) of Example 16 was dissolved in a mixed solvent including methanol and tetrahydrofuran (1 mL, 1:1) and then, the temperature was increased to 60° C. 18 mg (0.06 mmol) of Cesium carbonate was added thereto and the resultant mixture was stirred at 60° C. for 2 hours. Once the reaction was complete, the temperature was decreased to room temperature and an aqueous solution of ammonium chloride was added thereto. An extraction process was performed thereon three times using chloroform. The result was dried using anhydrous sodium sulfate, and then concentrated under reduced pressure. The obtained residue was purified using medium pressure liquid chromatography (MPLC) (chloroform:methanol=100:5 (v/v)), and the resulting solution was concentrated under reduced pressure to thereby obtain 10 mg of a target compound in the yield of 72%.

MS (ESI+, m/z): 517 [M+H]$^+$ $^1$H-NMR (300 MHz, DMSO-d$_6$): δ 11.90 (s, 1H), 9.49 (s, 1H), 8.51 (m, 3H), 7.48 (s, 1H), 7.46 (s, 1H), 7.39 (s, 1H), 7.07 (d, 1H), 6.65 (s, 1H), 5.19 (m, 1H), 4.62 (s, 2H), 4.14 (m, 1H), 3.46 (s, 2H), 3.16 (m, 2H), 2.83 (d, 2H), 1.945 (m, 4H), 1.11 (d, 2H), 0.93 (m, 4H), 0.64 (m, 2H).

Example 17: 5-chloro-N-(3-cyclopropyl-5-(((3R, 5S)-3,5-dimethylpiperazine-1-yl)methyl)phenyl)-4-(5-methoxy-6-methyl-1H-indole-3-yl)pyrimidine-2-amine

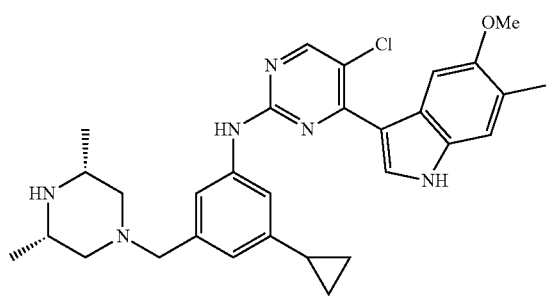

11 mg of a target compound was obtained in the yield of 13% in substantially the same manner as in Process 6) of Example 1, except that 50 mg (0.16 mmol) of 3-(2,5-dichloropyrimidine-4-yl)-5-methoxy-6-methyl-1H-indole was used instead of 3-(2,5-dichloropyrimidine-4-yl)-6-fluoro-1H-indole.

MS (ESI+, m/z): 531 [M+H]$^+$ $^1$H-NMR (300 MHz, DMSO-d$_6$): δ 11.64 (s, 1H), 9.45 (s, 1H), 8.41 (s, 1H), 8.27 (s, 1H), 7.85 (s, 1H), 7.38 (m, 2H), 7.22 (s, 1H), 6.61 (s, 1H), 3.50 (s, 3H), 2.72 (m, 2H), 2.65 (m, 2H), 2.27 (m, 4H), 1.65 (m, 1H), 1.59 (m, 2H), 1.21 (m, 2H), 1.07 (m, 6H), 0.82 (m, 2H), 0.51 (m, 2H).

Example 18: 3-(5-chloro-2-((3-cyclopropyl-5-(((3R, 5S)-3,5-dimethylpiperazine-1-yl)methyl)phenyl)amino)pyrimidine-4-yl)-6-methyl-1H-indole-5-ol

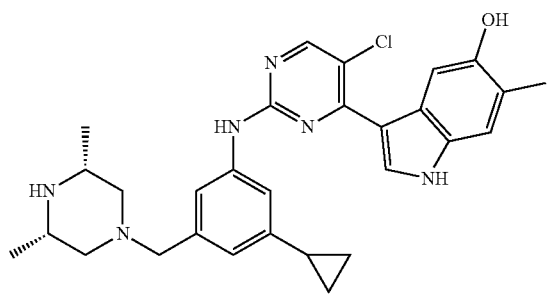

10 mg of a target compound was obtained in the yield of 15% in substantially the same manner as in Process 6) of Example 1, except that 39 mg (0.13 mmol) of 3-(2,5- dichloropyrimidine-4-yl)-6-methyl-1H-indole-5-ol was used instead of 3-(2,5-dichloropyrimidine-4-yl)-6-fluoro-1H-indole.

MS (ESI+, m/z): 517 [M+H]+

$^1$H-NMR (300 MHz, DMSO-$d_6$): δ 11.50 (s, 1H), 9.31 (s, 1H), 8.56 (s, 1H), 8.30 (s, 1H), 8.15 (s, 1H), 7.78 (s, 1H), 7.60 (s, 1H), 7.40 (s, 1H), 7.16 (s, 1H), 6.58 (s, 1H), 3.17-2.56 (m, 4H), 2.26 (m, 3H), 1.89 (m, 1H), 1.22 (m, 2H), 0.86 (m, 8H), 0.57 (m, 2H).

Example 19: 3-(5-chloro-2-((3-cyclopropyl-5-(((3R, 5S)-3,5-dimethylpiperazine-1-yl)methyl)phenyl)amino)pyrimidine-4-yl)-6-methylindoline-2-one

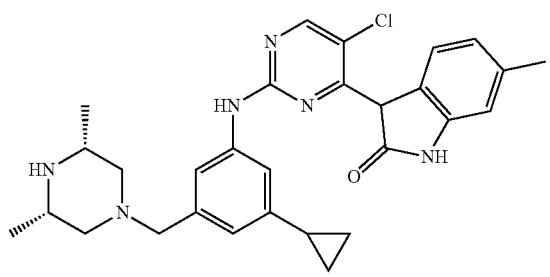

5 mg of a target compound was obtained in the yield of 3% in substantially the same manner as in Process 6) of Example 1, except that 70 mg (0.24 mmol) of 3-(2,5-dichloropyrimidine-4-yl)-6-methylindole-2-one was used instead of 3-(2,5-dichloropyrimidine-4-yl)-6-fluoro-1H-indole.

MS (ESI+, m/z): 517 [M+H]+

$^1$H-NMR (300 MHz, DMSO-$d_6$): δ 10.65 (s, 1H), 9.68 (s, 1H), 8.57 (s, 1H), 7.21 (m, 2H), 7.09 (m, 1H), 6.96 (m, 2H), 6.56 (s, 1H), 5.12 (s, 1H), 2.82 (m, 2H), 2.72 (m, 2H), 2.27 (s, 3H), 1.73 (m, 3H), 1.17 (m, 3H), 1.08 (m, 6H), 0.90 (m, 2H), 0.52 (m, 2H).

Example 20: 5-chloro-N-(3-cyclopropyl-5-(((3R, 5S)-3,5-dimethylpiperazine-1-yl)methyl)phenyl)-4-methoxy-6-(6-methyl-1H-indole-3-yl)pyrimidine-2-amine

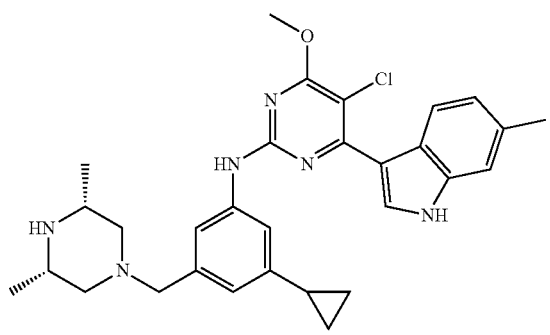

17 mg of a target compound was obtained in the yield of 17% in substantially the same manner as in Process 6) of Example 1, except that 60 mg (0.19 mmol) of 3-(2,5-dichloro-6-methoxypyrimidine-4-yl)-6-methyl-1H-indole was used instead of 3-(2,5-dichloropyrimidine-4-yl)-6-fluoro-1H-indole.

MS (ESI+, m/z): 531 [M+H]+

$^1$H-NMR (300 MHz, DMSO-$d_6$): δ 11.66 (s, 1H), 9.41 (s, 1H), 8.44 (d, 1H), 8.32 (s, 1H), 7.59 (s, 1H), 7.40 (s, 1H), 7.25 (s, 1H), 6.95 (d, 1H), 6.67 (s, 1H), 4.04 (s, 3H), 3.43 (s, 2H), 2.98 (m, 2H), 2.83 (m, 2H), 2.45 (s, 3H), 1.83 (m, 3H), 1.08 (m, 6H), 0.93 (m, 2H), 0.64 (m, 2H).

Example 21: 5-chloro-2-((3-cyclopropyl-5-(((3R, 5S)-3,5-dimethylpiperazine-1-yl)methyl)phenyl)amino)-6-(6-methyl-1H-indole-3-yl)pyrimidine-4-ol

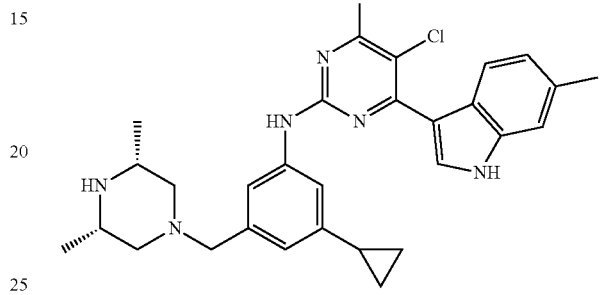

19 mg (0.04 mmol) of 5-chloro-N-(3-cyclopropyl-5-(((3R, 5S)-3,5-dimethylpiperazine-1-yl)methyl)phenyl)-4-methoxy-6-(6-methyl-1H-indole-3-yl)pyrimidine-2-amine prepared according to Example 20 was dissolved in 1 mL of ethanol, and then, 0.2 mL of hydrochloric acid was added thereto, followed by stirring at a temperature of 80° C. for 16 hours. Once the reaction was complete, the mixture was cooled to room temperature, and then, ethyl acetate and saturated sodium hydrogen carbonate were added thereto. An organic layer was separated therefrom, which was then dried using anhydrous sodium sulfate and concentrated under reduced pressure. The obtained residue was purified using column chromatography (chloroform:methanol=5:1 (v/v)), and the resulting solution was concentrated under reduced pressure to thereby obtain 1.4 mg of a target compound in the yield of 7%.

MS (ESI+, m/z): 517 [M+H]+

$^1$H-NMR (300 MHz, DMSO-$d_6$): δ 11.56 (s, 1H), 8.17 (m, 1H), 8.06 (d, 1H), 7.41 (s, 1H), 7.32 (s, 1H), 7.23 (s, 1H), 6.82 (d, 1H), 6.70 (s, 1H), 2.72 (m, 2H), 2.50 (m, 2H), 2.00 (s, 3H), 1.83 (m, 3H), 1.23 (m, 6H), 0.93 (m, 2H), 0.64 (m, 2H).

Example 22: 3-(5-chloro-2-((3-cyclopropyl-5-(((3R, 5S)-3,5-dimethylpiperazine-1-yl)methyl)phenyl)amino)pyrimidine-4-yl)-6-methyl-1H-indole-7-ol

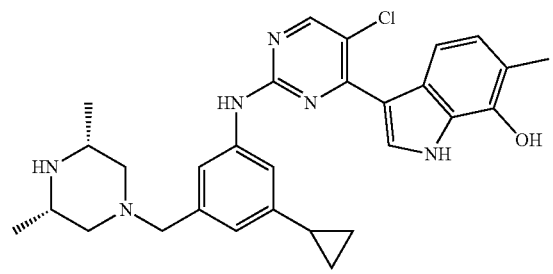

25 mg of a target compound was obtained in the yield of 41% in substantially the same manner as in Process 6) of Example 1, except that 50 mg (0.17 mmol) of 3-(2,5-dichloropyrimidine-4-yl)-6-methyl-1H-indole-7-ol was used instead of 3-(2,5-dichloropyrimidine-4-yl)-6-fluoro-1H-indole.

MS (ESI+, m/z): 517 [M+H]+

1H-NMR (300 MHz, DMSO-d6): δ 11.50 (bs, 1H), 9.45 (s, 1H), 8.95 (bs, 1H), 8.41 (s, 1H), 8.35 (s, 1H), 7.99 (d, 1H), 7.46 (s, 1H), 7.39 (s, 1H), 6.85 (d, 1H), 6.62 (s, 1H), 3.34 (s, 2H), 2.73 (m, 2H), 2.63 (m, 2H), 2.28 (s, 3H), 1.83 (m, 1H), 1.44 (t, 2H), 0.92 (m, 9H), 0.61 (m, 2H).

Example 23: 2-((5-chloro-4-(6-methyl-1H-indole-3-yl)pyrimidine-2-yl)amino)-4-cyclopropyl-6-(((3R, 5S)-3,5-dimethylpiperazine-1-yl)methyl)phenol

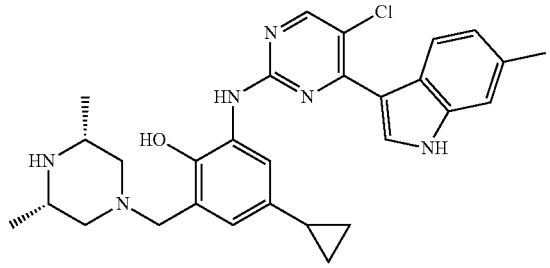

5 mg of a target compound was obtained in the yield of 5% in substantially the same manner as in Process 6) of Example 1, except that 56 mg (0.20 mmol) of 2-amino-4-cyclopropyl-6-(((3R, 5S)-3,5-dimethylpiperazine-1-yl)methyl)phenol was used instead of 3-cyclopropyl-5-(((3R, 5S)-3,5-dimethylpiperazine-1-yl)methyl)aniline, and 85 mg (0.31 mmol) of 3-(2,5-dichloropyrimidine-4-yl)-6-methyl-1H-indole was used instead of 3-(2,5-dichloropyrimidine-4-yl)-6-fluoro-1H-indole.

MS (ESI+, m/z): 517 [M+H]+

1H-NMR (300 MHz, DMSO-d6): δ 11.72 (s, 1H), 8.38 (m, 2H), 8.15 (d, 1H), 8.08 (s, 1H), 7.55 (s, 1H), 7.22 (s, 1H), 6.82 (d, 1H), 6.50 (s, 1H), 3.60 (s, 2H), 2.70 (d, 4H), 2.46 (s, 3H), 1.74 (m, 1H), 1.63 (t, 2H), 0.84 (d, 6H), 0.79 (m, 2H), 0.50 (m, 2H).

Example 24: 4-((5-chloro-4-(6-methyl-1H-indole-3-yl)pyrimidine-2-yl)amino)-2-cyclopropyl-6-(((3R, 5S)-3,5-dimethylpiperazine-1-yl)methyl)phenol

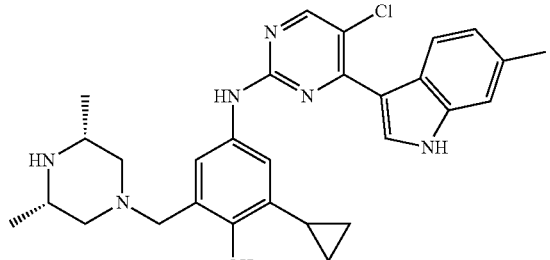

200 mg of a target compound was obtained in the yield of 53% in substantially the same manner as in Process 6) of Example 1, except that 200 mg (0.73 mmol) of 4-amino-2-cyclopropyl-6-(((3R, 5S)-3,5-dimethylpiperazine-1-yl)methyl)phenol was used instead of 3-cyclopropyl-5-(((3R, 5S)-3,5-dimethylpiperazine-1-yl)methyl)aniline, and 303 mg (1.09 mmol) of 3-(2-chloro-5-methylpyrimidine-4-yl)-6-methyl-1H-indole was used instead of 3-(2,5-dichloropyrimidine-4-yl)-6-fluoro-1H-indole.

MS (ESI+, m/z): 517 [M+H]+

1H-NMR (300 MHz, DMSO-d6): δ 11.72 (s, 1H), 11.05 (s, 1H), 9.09 (s, 1H), 8.40-8.32 (m, 4H), 7.26 (s, 2H), 6.84 (m, 2H), 3.59 (m, 2H), 2.77 (d, 4H), 2.41 (s, 3H), 2.11 (m, 1H), 1.60 (t, 2H), 0.92 (d, 6H), 0.87 (m, 2H), 0.58 (m, 2H).

Example 25: (R)-5-chloro-N-(3-cyclopropyl-5-((3,3,5-trimethylpiperazine-1-yl)methyl)phenyl)-4-(6-methyl-1H-indole-3-yl)pyrimidine-2-amine Process 1) (3-amino-5-cyclopropylphenyl)methanol

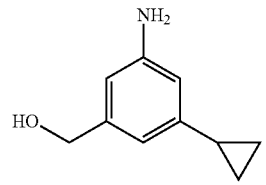 [SMILES: Nc1cc(CO)cc(C2CC2)c1]

5.8 g of a target compound was obtained in the yield of 95% in substantially the same manner as in Process 5) of Example 1, except that 7.2 g (37.27 mmol) of (3-cyclopropyl-5-nitrophenyl)methanol was used instead of (3R, 5S)-1-(3-cyclopropyl-5-nitrobenzyl)-3,5-dimethylpiperazine.

1H-NMR (300 MHz, DMSO-d6): δ6.31 (s, 1H), 6.18 (s, 1H), 6.13 (s, 1H), 4.94 (m, 3H), 4.28 (d, 2H), 1.73 (m, 1H), 0.87 (m, 2H), 0.56 (m, 2H).

Process 2) (3-((5-chloro-4-(6-methyl-1H-indole-3-yl)pyrimidine-2-yl)amino)-5-cyclopropylphenyl)methanol

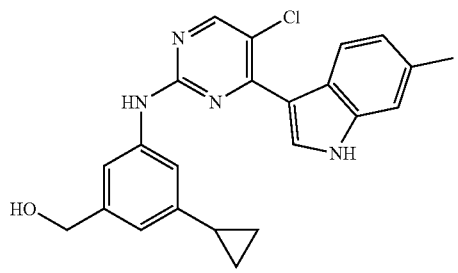 [SMILES: Cc1ccc2c(-c3nc(Nc4cc(CO)cc(C5CC5)c4)ncc3Cl)c[nH]c2c1]

3.5 g of a target compound was obtained in the yield of 49% in substantially the same manner as in Process 6) of Example 1, except that 2.9 g (17.77 mmol) of (3-amino-5-cyclopropylphenyl)methanol was used instead of 3-cyclopropyl-5-(((3R, 5S)-3,5-dimethylpiperazine-1-yl)methyl)aniline, and 7.4 g (26.65 mmol) of 3-(2,5-dichloropyrimidine-4-yl)-6-methyl-1H-indole was used instead of 3-(2,5-dichloropyrimidine-4-yl)-6-fluoro-1H-indole.

1H-NMR (300 MHz, DMSO-d6): δ 11.78 (s, 1H), 9.48 (s, 1H), 8.50 (m, 3H), 7.53 (s, 1H), 7.38 (s, 1H), 7.28 (s, 1H), 6.96 (d, 1H), 6.67 (s, 1H), 5.10 (t, 1H), 4.42 (d, 1H), 2.43 (s, 3H), 1.84 (m, 1H), 0.93 (m, 2H), 0.65 (m, 2H).

Process 3) 3-((5-chloro-4-(6-methyl-1H-indole-3-yl)pyrimidine-2-yl)amino)-5-cyclopropylbenzaldehyde

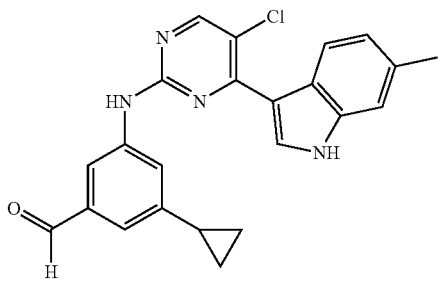 [SMILES: Cc1ccc2c(-c3nc(Nc4cc(C=O)cc(C5CC5)c4)ncc3Cl)c[nH]c2c1]

5.67 g (14.00 mmol) of (3-((5-chloro-4-(6-methyl-1H-indole-3-yl)pyrimidine-2-yl)amino)-5-cyclopropylphenyl)methanol prepared according to Process 2) of Example 25 was dissolved in 200 mL of methylene chloride, and then, 14.3 g (140.00 mmol) of manganese dioxide was added thereto. The resultant mixture was stirred at room temperature for 18 hours. When the reaction was completed, the resultant mixture was filtered through a filter filled with celite and washed with methylene chloride. The obtained organic layer was concentrated under reduced pressure. The obtained residue was purified using MPLC (ethyl acetate:hexane=1:4 (v/v)), and the resulting solution was concentrated under reduced pressure to thereby obtain 2.1 g of a target compound in the yield of 37%.

$^1$H-NMR (300 MHz, DMSO-$d_6$): δ 11.81 (s, 1H), 9.90 (s, 1H), 9.78 (s, 1H), 8.50 (m, 3H), 8.15 (s, 1H), 7.81 (s, 1H), 7.25 (d, 2H), 6.94 (d, 2H), 2.42 (s, 3H), 1.97 (m, 1H), 1.02 (m, 2H), 0.75 (m, 2H).

Process 4) Preparation of (R)-5-chloro-N-(3-cyclopropyl-5-((3,3,5-trimethylpiperazine-1-yl)methyl)phenyl)-4-(6-methyl-1H-indole-3-yl)pyrimidine-2-amine

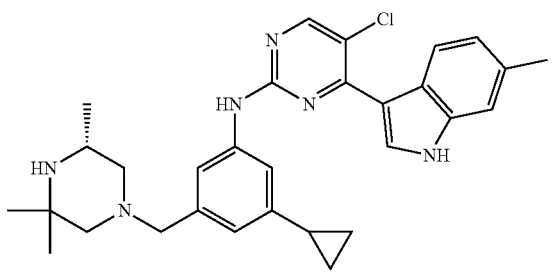

140 mg (0.35 mmol) of 3-((5-chloro-4-(6-methyl-1H-indole-3-yl)pyrimidine-2-yl)amino)-5-cyclopropylbenzaldehyde prepared according to Process 3) of Example 25 and 140 mg (0.70 mmol) of (R)-2,2,6-trimethylpiperazine hydrochloride were dissolved in 2 mL of 1,2-dichloroethane, and 200 mg (0.75 mmol) of sodiumtriacethoxy borohydride and 0.3 mL (1.74 mmol) of diisopropylamine were added thereto. The mixture was stirred at room temperature for 3 hours. When the reaction was completed, methylene chloride and a saturated aqueous sodium hydrogen carbonate solution were added dropwise thereto. An organic layer was extracted therefrom, and the organic layer was washed with saline water, dried using anhydrous sodium sulfate, and concentrated under reduced pressure. The obtained residue was purified using MPLC (methylenechloride:methanol=25:1 (v/v)), and the resulting solution was concentrated under reduced pressure to thereby obtain 140 mg of a target compound in the yield of 78%.

MS (ESI+, m/z): 515 [M+H]$^+$ $^1$H-NMR (300 MHz, DMSO-$d_6$): δ 11.77 (s, 1H), 9.47 (s, 1H), 8.48 (m, 3H), 7.57 (s, 1H), 7.35 (s, 1H), 7.28 (s, 1H), 6.94 (d, 1H), 6.64 (s, 1H), 3.38 (q, 2H), 2.95 (m, 1H), 2.70 (d, 1H), 2.43 (s, 3H), 1.84 (m, 1H), 1.59 (m, 2H), 1.23 (d, 1H), 1.12 (s, 3H), 0.94 (m, 2H), 0.63 (m, 2H).

Example 26: ((2R, 6R)-4-(3-((5-chloro-4-(6-methyl-1H-indole-3-yl)pyrimidine-2-yl)amino)-5-cyclopropylbenzyl)-6-methylpiperazine-2-yl)methanol

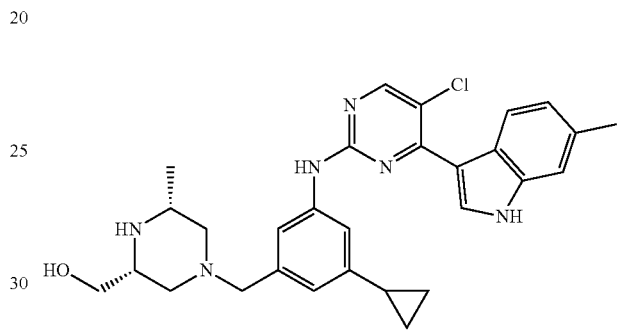

22 mg of a target compound was obtained in the yield of 24% in substantially the same manner as in Process 4) of Example 25, except that 55 mg (0.27 mmol) of ((2R, 6R)-6-methylpiperazine-2-yl)methanolhydrochloride was used instead of (R)-2,2,6-trimethylpiperazinehydrochloride.

MS (ESI+, m/z): 517 [M+H]$^+$ $^1$H-NMR (300 MHz, DMSO-$d_6$): δ 11.80 (s, 1H), 9.49 (s, 1H), 8.48 (m, 3H), 7.50 (s, 1H), 7.40 (s, 1H), 7.33 (s, 1H), 6.95 (d, 1H), 6.65 (s, 1H), 4.99 (m, 1H), 4.10 (m, 1H), 3.42 (s, 2H), 3.16 (d, 2H), 2.97 (m, 2H), 2.80 (m, 2H), 2.43 (s, 3H), 1.85 (m, 3H), 1.23 (m, 2H), 1.04 (d, 3H), 0.94 (m, 2H), 0.65 (m, 2H).

Example 27: (R)-5-chloro-N-(3-cyclopropyl-5-((5-methyl-4,7-diazaspiro[2.5]octan-7-yl)methyl)phenyl)-4-(6-methyl-1H-indole-3-yl)pyrimidine-2-amine

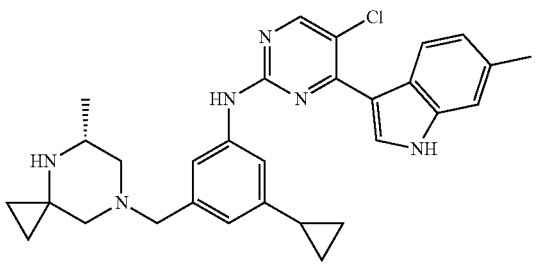 [SMILES: Cc1ccc2c(-c3nc(Nc4cc(CN5C[C@@H](C)NC6(CC6)C5)cc(C5CC5)c4)ncc3Cl)c[nH]c2c1]

150 mg of a target compound was obtained in the yield of 60% in substantially the same manner as in Process 4) of Example 25, except that 188 mg (1.49 mmol) of (R)-5- methyl-4,7-diazaspiro[2.5]octanhydrochloride was used instead of (R)-2,2,6-trimethylpiperazinehydrochloride.

$^1$H-NMR (300 MHz, DMSO-d$_6$): δ 11.77 (s, 1H), 9.46 (s, 1H), 8.47 (m, 3H), 7.47 (s, 1H), 7.40 (s, 1H), 7.28 (s, 1H), 6.95 (d, 1H), 6.64 (s, 1H), 2.71 (d, 2H), 2.62 (d, 2H), 2.42 (s, 3H), 1.87 (m, 1H), 1.50 (q, 2H), 1.23 (q, 2H), 0.92 (m, 8H), 0.62 (m, 2H).

Example 28: 5-chloro-N-(3-cyclopropyl-5-(((3R, 5R)-3,5-dimethylpiperazine-1-yl)methyl)phenyl)-4-(6-methyl-1H-indole-3-yl)pyrimidine-2-amine

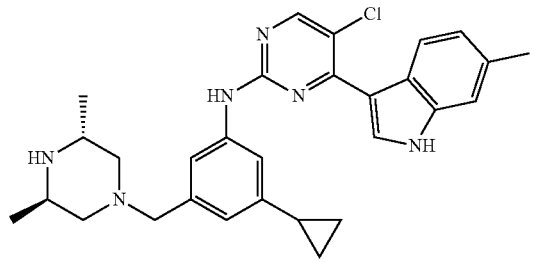

17 mg of a target compound was obtained in the yield of 9% in substantially the same manner as in Process 4) of Example 25, except that 149 mg (0.80 mmol) of (2R, 6R)-2,6-dimethylpiperazine hydrochloride was used instead of (R)-2,2,6-trimethylpiperazine hydrochloride.

MS (ESI+, m/z): 501 [M+H]$^+$ $^1$H-NMR (300 MHz, DMSO-d$_6$): δ 11.80 (s, 1H), 9.15 (s, 1H), 8.46 (m, 3H), 7.66 (s, 1H), 7.35 (s, 1H), 7.28 (s, 1H), 6.95 (d, 1H), 6.63 (s, 1H), 3.51 (d, 2H), 2.43 (s, 3H), 2.25 (m, 2H), 1.85 (m, 1H), 1.23 (s, 2H), 0.91 (m, 4H), 0.62 (m, 2H).

Example 29: 5-chloro-N-(3-cyclopropyl-5-(((3S, 5S)-3,5-dimethylpiperazine-1-yl)methyl)phenyl)-4-(6-methyl-1H-indole-3-yl)pyrimidine-2-amine

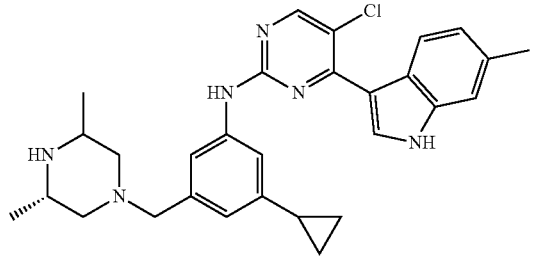

25 mg of a target compound was obtained in the yield of 15% in substantially the same manner as in Process 4) of Example 25, except that 75 mg (0.66 mmol) of (2S, 6S)-2,6-dimethylpiperazinehydrochloride was used instead of (R)-2,2,6-trimethylpiperazinehydrochloride.

MS (ESI+, m/z): 501 [M+H]$^+$ $^1$H-NMR (300 MHz, DMSO-d$_6$): δ 11.76 (s, 1H), 9.46 (s, 1H), 8.46 (m, 3H), 7.55 (s, 1H), 7.35 (s, 1H), 7.27 (s, 1H), 6.94 (d, 1H), 6.63 (s, 1H), 3.59 (t, 2H), 3.05 (m, 2H), 2.32 (d, 2H), 1.89 (m, 2H), 1.75 (m, 1H), 1.01 (d, 6H), 0.91 (m, 2H), 0.62 (m, 2H).

Example 30: 5-chloro-N-(3-cyclopropyl-5-(((3R, 5S)-3,4,5-trimethylpiperazine-1-yl)methyl)phenyl)-4-(6-methyl-1H-indole-3-yl)pyrimidine-2-amine

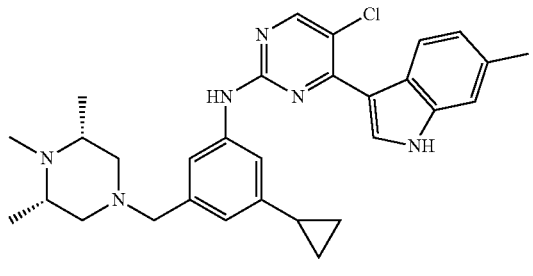

70 mg of a target compound was obtained in the yield of 79% in substantially the same manner as in Process 4) of Example 25, except that 168 mg (0.70 mmol) of (2R, 6S)-1,2,6-trimethylpiperazinetrifluoroacetate was used instead of (R)-2,2,6-trimethylpiperazinehydrochloride.

MS (ESI+, m/z): 515 [M+H]$^+$ $^1$H-NMR (300 MHz, DMSO-d$_6$): δ 11.76 (s, 1H), 9.46 (s, 1H), 8.46 (m, 3H), 7.48 (s, 1H), 7.40 (s, 1H), 7.28 (s, 1H), 6.95 (d, 1H), 6.64 (s, 1H), 4.34 (m, 1H), 3.47 (m, 1H), 2.63 (m, 2H), 2.43 (s, 3H), 2.15 (m, 2H), 1.82 (m, 2H), 1.08 (m, 8H), 0.62 (m, 2H).

Example 31: (2R, 6S)-4-(3-((5-chloro-4-(6-methyl-1H-indole-3-yl)pyrimidine-2-yl)amino)-5-cyclopropylbenzyl)-2,6-dimethylpiperazine-1-ol

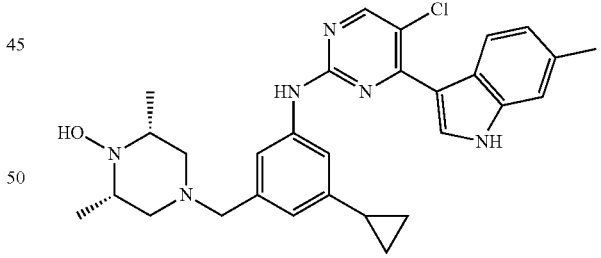

60 mg of a target compound was obtained in the yield of 94% in substantially the same manner as in Process 4) of Example 25, except that 62 mg (0.37 mmol) of (2R,6S)-2,6-dimethylpiperazin-1-olhydrochloride was used instead of (R)-2,2,6-trimethylpiperazinehydrochloride.

MS (ESI+, m/z): 517 [M+H]$^+$ $^1$H-NMR (300 MHz, DMSO-d$_6$): δ 11.77 (s, 1H), 9.48 (s, 1H), 8.47 (m, 3H), 7.67 (s, 1H), 7.47 (s, 1H), 7.41 (s, 1H), 7.28 (s, 1H), 6.95 (d, 1H), 6.63 (s, 1H), 3.31 (s, 2H), 2.69 (d, 2H), 2.43 (s, 3H), 1.81 (m, 3H), 1.05 (t, 2H), 0.95 (m, 8H), 0.62 (m, 2H).

Example 32: (2R, 6S)-4-(3-cyclopropyl-5-((4-(6-methyl-1H-indol-3-yl)pyrimidine-2-yl)amino)benzyl)-2,6-dimethylpiperazine-1-ol

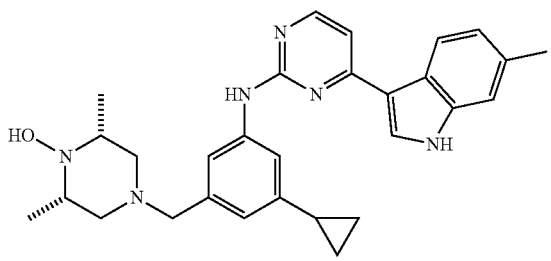 [SMILES: Cc1ccc2c(-c3ccnc(Nc4cc(CN5C[C@@H](C)N(O)[C@@H](C)C5)cc(C5CC5)c4)n3)c[nH]c2c1]

1.5 g of a target compound was obtained in the yield of 51% in substantially the same manner as in Example 25, except that, in Process 4) of Example 25, 2.5 g (12.16 mmol) (2R, 6S)-2,6-dimethylpiperazine-1-olhydrochloride was used instead of (R)-2,2,6-trimethylpiperazinehydrochloride, and 2.24 g (6.08 mmol) of 3-cyclopropyl-5-((4-(6-methyl-1H-indole-3-yl)pyrimidine-2-yl)amino)benzaldehyde was used instead of 3-((5-chloro-4-(6-methyl-1H-indole-3-yl)pyrimidine-2-yl)amino)-5-cyclopropylbenzaldehyde.

MS (ESI$^+$, m/z): 483 [M+H]$^+$ $^1$H-NMR (300 MHz, DMSO-d$_6$): δ 11.63 (bs, 1H), 9.23 (s, 1H), 8.45 (d, 1H), 8.29 (m, 1H), 8.20 (s, 1H), 7.66 (s, 1H), 7.51 (d, 2H), 7.22 (m, 2H), 6.96 (d, 1H), 6.58 (s, 1H), 2.73 (m, 2H), 2.55 (m, 4H), 1.88 (m, 1H), 1.82 (m, 2H), 0.96 (m, 8H), 0.64 (m, 2H).

EXPERIMENTAL EXAMPLES

The kinase inhibitory activity and cell growth inhibitory activity of the foregoing compounds prepared in the Examples were evaluated. The results thereof are as follows.

Experimental Example 1: Evaluation of Kinase Inhibitory Activity

The inhibitory activity of some of the compounds described above against FLT3-ITD, FLT3 wild type (WT), VEGFR2 (KDR), and SYK kinase was measured.

The inhibitory activity of the compounds against mutant proteins, such as FLT3 WT and ITD, was evaluated based on the LanthaScreen technology developed by Thermo Fisher Scientific Inc. This assay is based on the binding of Alexa Fluor® 647-labeled, ATP-competitive kinase inhibitor (kinase tracer-236) to kinase, and signals of fluorescence resonance energy transfer (FRET) were measured in the presence of europium-conjugated antibody. This experiment was carried out on a 384-well plate in conditions including 50 mM HEPES pH 7.5, 0.01% BRIJ-35, 10 mM MgCl$_2$, 1 mM EGTA, and 1% DMSO. After measuring the background signal in the absence of proteins such as FLT3 or FLT3-ITD and measuring the non-inhibition signal by adding only the solvent (1% DMSO), an evaluation compound was used at a set concentration (for example, 50 nM to 0.05 nM, 1:10 dilution) to calculate the kinase inhibitory activity of the evaluation compound as IC$_{50}$. The results are shown in Table 2 below.

TABLE 2

Kinase Inhibitory activity of pyrimidine compound on FLT3 ITD and WT

| Compound | FLT3 ITD (IC$_{50}$, nM) | FLT3 WT (IC$_{50}$, nM) |
|---|---|---|
| Example 2 | 1.5 | 1.9 |
| Example 3 | 8.1 | — |
| Example 4 | 3.6 | — |
| Example 5 | 7.2 | — |
| Example 6 | 1.8 | — |
| Example 8 | 1.8 | 1.1 |
| Example 10 | 3.6 | — |
| Example 12 | 2.5 | 1.2 |
| Example 13 | 8.7 | — |
| Example 16 | 0.5 | 0.4 |
| Example 17 | >50 | 9.5 |
| Example 18 | 13 | 3.7 |
| Example 19 | >50 | — |
| Example 22 | 2.4 | — |
| Example 23 | >50 | 0.4 |
| Example 25 | 20 | 2.3 |
| Example 26 | 2.3 | 1.5 |
| Example 31 | 6.9 | — |

As shown in Table 2, the compound of the present disclosure showed excellent kinase inhibitory activity against FLT3 ITD and WT.

The SYK inhibitory activity of the compounds was evaluated based on z-LYTE technology developed by Thermo Fisher Scientific Inc. According to this evaluation method, signals of the fluorescence of FRET-peptides are measured, wherein fluorescence of a FRET-peptide which is phosphorylated by the binding of the compound to the target and fluorescence of a non-phosphorylated peptide are measured to identify an activity with respect to kinase. This experiment was carried out on a 384-well plate in conditions including 50 mM HEPES pH 7.5, 0.01% BRIJ-35, 10 mM MgCl$_2$, 1 mM EGTA, and 1% DMSO. The background signal was measured in the absence of proteins; a non-inhibitory signal was measured only when the solvent (1% DMSO) was added; and an evaluation compound was used at a concentration of 100 nM to calculate the SYK inhibitory activity of the evaluation compound as a percentage (%). A z-lyte kinase assays kit (Life Technologies, PV 3190) was used for VEGFR and tests were performed by Life Technologies Inc. Table 3 shows the inhibitory activity of the compound against the corresponding kynase as a percentage (%) when the concentration of the compound was 100 nM.

TABLE 3

Inhibitory activity (percentage, %) of pyrimidine compound for VEGFR2 and SYK kinase

| Compound | VEGFR2 (% inhibition) | SYK (% inhibition) |
|---|---|---|
| Example 1 | 95 | 73 |
| Example 5 | 71 | 78 |
| Example 8 | 100 | 95 |

As shown in Table 3, the compounds according to the present disclosure have excellent VEGFR2 and SYK kinase inhibitory activity.

Experimental Example 2: Evaluation of Cell Growth Inhibitory Activity

The human acute myelogenous leukemia (ALL) cell line MOLM-13 (DSMZ no. ACC 554) was incubated in RPMI1640 medium supplemented with 20% heat-inactivated FBS at a temperature of 37° C. The incubated cell line was prepared in an amount of 2.0×10⁴ cells/100 μL, and then plated on a 96-well plate. The RPMI1640 medium was serially diluted with the test compounds at a concentration in a range of 1 μM to 0.01 nM at a ratio of 1:10. Subsequently, incubation was performed thereon for three days. For the human acute myelogenous leukemia cell line MV-4-11 cell line (ATCC® CRL-9591™), the cells were incubated at a temperature of 37° C. in IMDM medium supplemented with 10% FBS. The incubated cell line was prepared in an amount of 2×10⁴ cells/100 μL, and then plated on a 96-well plate. The IMDM medium was treated with cascade dilution of three test compounds at a concentration in a range of 1 μM to 0.01 nM at a rate of 1/10. Subsequently, incubation was performed thereon for three days. MTS test was performed to measure cell viability, and the growth inhibition ($GI_{50}$) value of the cell line was calculated using GraphPad Prism software. The results for each cell line are shown in Table 4 below.

TABLE 4

| Cell growth inhibitory activity of pyrimidine compound | | |
|---|---|---|
| Compound | MOLM-13($GI_{50}$, nM) | MV-4-11($GI_{50}$, nM) |
| Example 1 | 4.0 | 1.2 |
| Example 2 | 6.2 | 3.5 |
| Example 3 | 0.4 | 0.3 |
| Example 4 | 0.7 | 1.7 |
| Example 5 | 0.8 | 0.5 |
| Example 8 | 5.2 | 1.3 |
| Example 10 | 5.0 | 2.8 |
| Example 12 | 21 | 11 |
| Example 13 | 2.6 | 2.1 |
| Example 25 | 8.5 | 9.3 |
| Example 26 | 6.1 | 22 |
| Example 28 | 0.8 | <0.01 |

As shown in Table 4, the compound of the present disclosure was found to have excellent growth inhibitory activity on an acute myelogenous leukemia (ALL) cell line.

Experimental Example 3: Evaluation of Pharmacokinetic Profile

After test substances were formulated by using the selected solvents, they were administered orally (p.o.) and intravenously (iv) once for each and a certain amount of blood was taken at a predetermined time, and plasma was isolated from the blood and a concentration analysis was performed thereon by LC-MS/MS. The AUG (drug concentration and an area under the curve) was calculated according to the linear-log trapezoidal summation formula by using the non-compartment analysis of the WinNonlin program through the plasma concentration curves over time. The bioavailability (BA) was calculated by applying the calculated AUG value to the following formula. BA (%)=(AUG p.o./AUG i.v.)×(Dose i.v./Dose p.o.)×100

TABLE 5

| | Bioavailability and area under curve of pyrimidine compound | |
|---|---|---|
| | Bioavailability of mice (%) | Area under the curve (AUC) of mice (Unit: ng · hr/mL) |
| Example 4 | 7.4 | 184.5 |

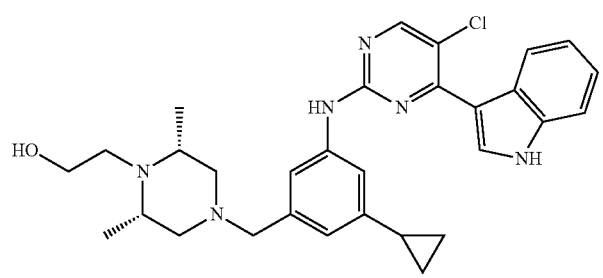 [SMILES: C[C@@H]1CN(Cc2cc(Nc3ncc(Cl)c(-c4c[nH]c5ccccc45)n3)cc(C3CC3)c2)C[C@H](C)N1CCO]

| Control Compound 1 | 6.6 | 95.5 |

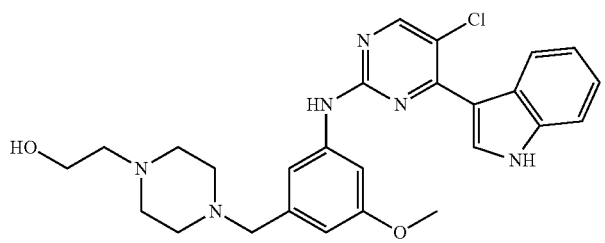 [SMILES: COc1cc(CN2CCN(CCO)CC2)cc(Nc2ncc(Cl)c(-c3c[nH]c4ccccc34)n2)c1]

TABLE 5-continued
Bioavailability and area under curve of pyrimidine compound
| | Bioavailability of mice (%) | Area under the curve (AUC) of mice (Unit: ng · hr/mL) |
|---|---|---|
| Control Compound 2 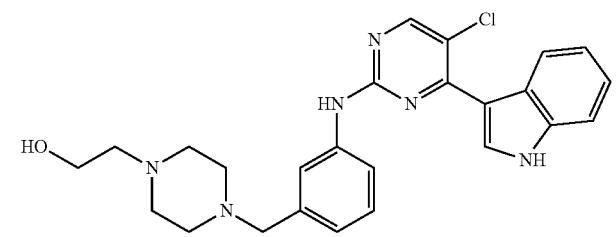 [SMILES: OCCN1CCN(Cc2cccc(Nc3ncc(Cl)c(-c4c[nH]c5ccccc45)n3)c2)CC1] | 6.7 | 109.7 |
TABLE 6
Bioavailability and area under curve of pyrimidine compound
| | Bioavailability of mice (%) | Area under the curve (AUC) of mice (Unit: ng · hr/mL) |
|---|---|---|
| Example 25 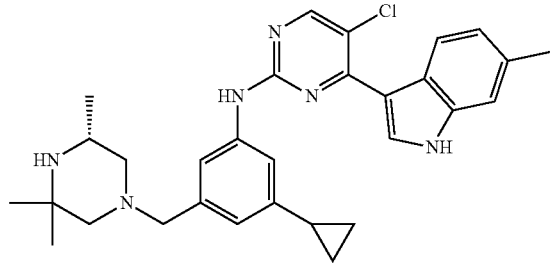 | 21.2 | 21780.9 |
| Control Compound 3 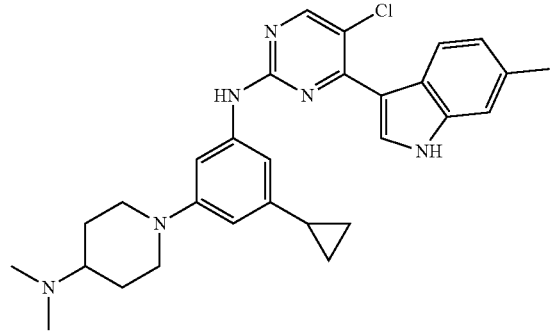 | 27.3 | 2268 |

TABLE 6-continued

Bioavailability and area under curve of pyrimidine compound

|  | Bioavailability of mice (%) | Area under the curve (AUC) of mice (Unit: ng · hr/mL) |
|---|---|---|
| Control Compound 4 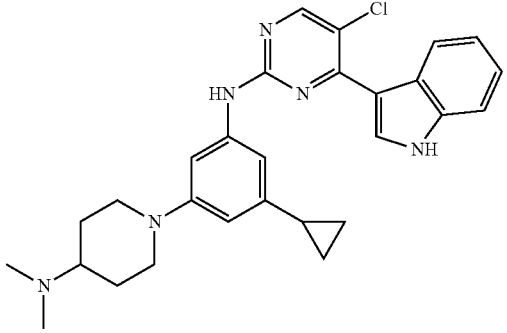 [SMILES: CN(C)C1CCN(c2cc(Nc3ncc(Cl)c(-c4c[nH]c5ccccc45)n3)cc(C3CC3)c2)CC1] | 27 | 518.2 |
| Control Compound 5 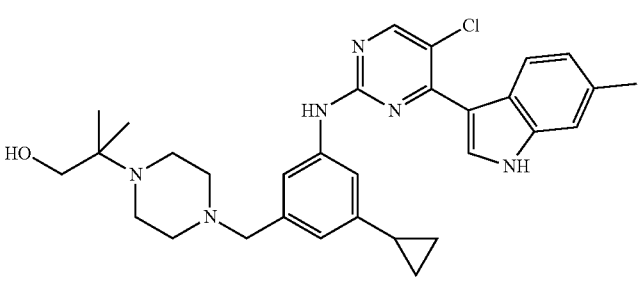 [SMILES: Cc1ccc2c(-c3nc(Nc4cc(CN5CCN(C(C)(C)CO)CC5)cc(C5CC5)c4)ncc3Cl)c[nH]c2c1] | 25.6 | 1219 |

As shown in Table 5 and Table 6, the compound according to an embodiment of the present disclosure showed better absorbability characteristics suitable for oral administration, such as bioavailability and area under curve, than control compounds having chemical structures being similar to the compound.

Experimental Example 4: Microsomal Stability Measurement Method

To confirm the reactivity of the test substances with intra-hepatic CYP450 enzymes, 5 µM test substances and 1 mg/ml human liver microsomes were incubated for 1 hour at a temperature of 37° C. in the presence of an NADPH regenerating system. After 1 hour, acetonitrile was added to terminate the reaction, and the supernatant obtained by centrifugation was analyzed by HPLC. The remaining amount % was calculated using the following equation using the value of the reacted sample for 1 hour relative to the value of the 0-minute sample as the peak value obtained as an analysis result. (Peak value of the sample reacted for 1 hour/peak value of the sample at 0 minutes)×100=residual amount %.

TABLE 7

Microsomal stability of pyrimidine compound

|  | Human microsomal stability (%) | Mice microsomal stability (%) |
|---|---|---|
| Example 27 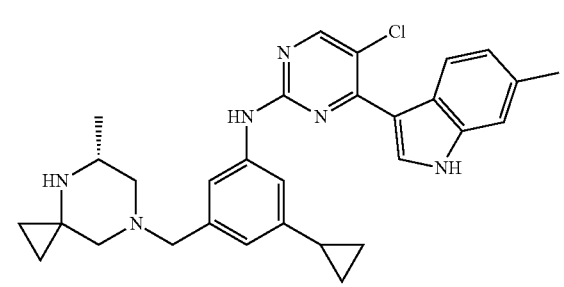 [SMILES: Cc1ccc2c(-c3nc(Nc4cc(CN5C[C@@H](C)NC6(CC6)C5)cc(C5CC5)c4)ncc3Cl)c[nH]c2c1] | 72 | 69 |

TABLE 7-continued

Microsomal stability of pyrimidine compound

| | Human microsomal stability (%) | Mice microsomal stability (%) |
| --- | --- | --- |
| Control Compound 6 | 49 | 29 |

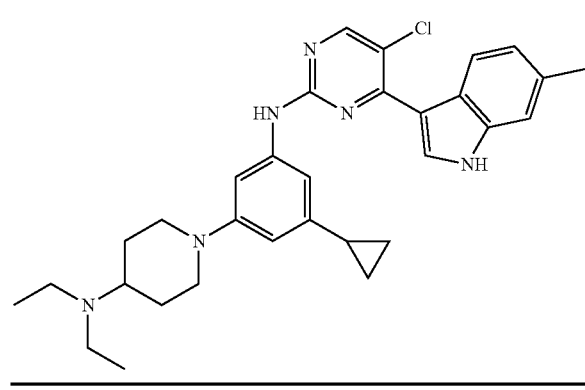

As shown in Table 7, the compound according to an embodiment of the present disclosure has improved microsomal stability compared to a control compound having a chemical structure being similar thereto.

Through the example data, it can be seen that the compounds according to an embodiment of the present disclosure were found to have better pharmacokinetic properties than the control compounds having substituents being similar thereto and comparable levels of steric hindrance.

The compound according to one aspect of the present disclosure is excellent in FLT3 inhibitory activity and thus is effectively used for the prevention or treatment of cell proliferative diseases caused by abnormal FLT3 activity such as cancer, for example, leukemia.

While this disclosure has been particularly shown and described with reference to example embodiments thereof, it will be understood by those skilled in the art that various changes in form and details may be made therein without departing from the spirit and scope of the disclosure as defined by the appended claims. The example embodiments should be considered in descriptive sense only and not for purposes of limitation. Therefore, the scope of the disclosure is defined not by the detailed description of the disclosure but by the appended claims, and all differences within the scope will be construed as being included in the present disclosure.

What is claimed is:

1. A compound selected from:

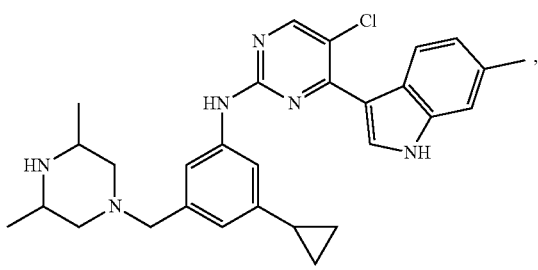

a stereoisomer thereof, or a mixture of stereoisomers thereof, or a pharmaceutically acceptable salt and/or solvate thereof.

2. The compound of claim 1, wherein the compound is:

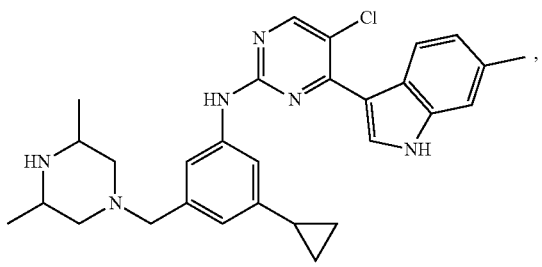

or a pharmaceutically acceptable salt thereof.

3. The compound of claim 1, wherein the compound is

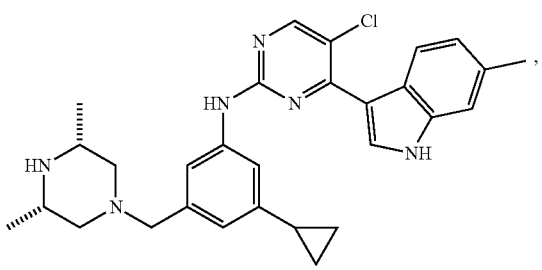

or a pharmaceutically acceptable salt thereof.

4. The compound of claim 1, wherein the compound is:

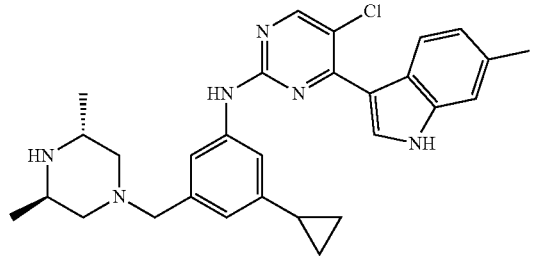

or a pharmaceutically acceptable salt thereof.

5. A pharmaceutical composition comprising a compound selected from:

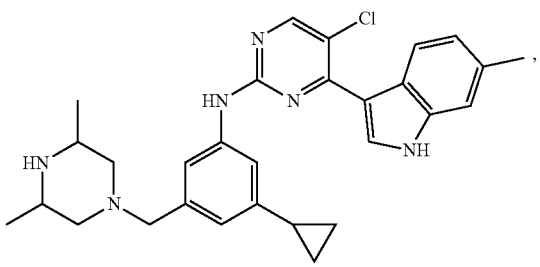

a stereoisomer thereof, or a mixture of stereoisomers thereof, or a pharmaceutically acceptable salt and/or solvate thereof.

6. The pharmaceutical composition of claim 5, wherein the compound is:

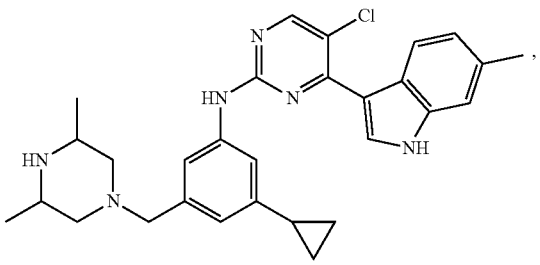

or a pharmaceutically acceptable salt thereof.

7. The pharmaceutical composition of claim 5, wherein the compound is:

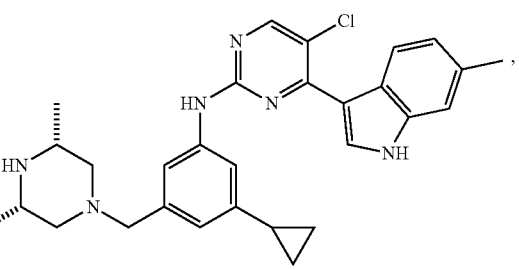

or a pharmaceutically acceptable salt thereof.

8. The pharmaceutical composition of claim 5, wherein the compound is:

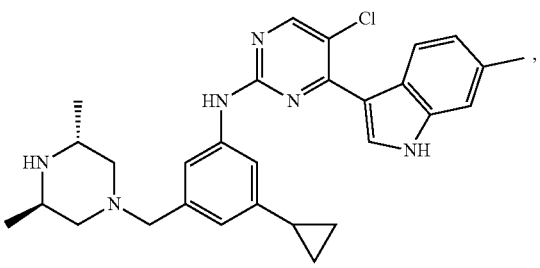

or a pharmaceutically acceptable salt thereof.

* * * * *